United States Patent
Bigge et al.

[11] Patent Number: 6,124,317
[45] Date of Patent: Sep. 26, 2000

[54] 2-SUBSTITUTED PIPERIDINE ANALOGS AND THEIR USE AS SUBTYPE-SELECTIVE NMDA RECEPTOR ANTAGONISTS

[75] Inventors: Christopher F. Bigge, Ann Arbor, Mich.; John F. W. Keana, Eugene, Oreg.; Sui Xiong Cai, Foothill, Calif.; Eckard Weber, Laguna Beach, Calif.; Richard Woodward, Aliso Viejo, Calif.; Nancy C. Lan, South Pasadena, Calif.; Anthony P. Guzikowski, Eugene, Oreg.

[73] Assignees: Warner-Lambert Company, Morris Plains, N.J.; Cocensys, Inc., Irvine, Calif.

[21] Appl. No.: 09/091,593

[22] PCT Filed: Dec. 20, 1996

[86] PCT No.: PCT/US96/20767

§ 371 Date: Nov. 18, 1998

§ 102(e) Date: Nov. 18, 1998

[87] PCT Pub. No.: WO97/23215

PCT Pub. Date: Jul. 3, 1997

Related U.S. Application Data

[60] Provisional application No. 60/009,182, Dec. 22, 1995.

[51] Int. Cl.⁷ ..................................................... A01N 43/40
[52] U.S. Cl. .......................... 514/317; 514/331; 546/229; 546/236
[58] Field of Search ................................... 546/229, 236; 514/331, 317

[56] References Cited

U.S. PATENT DOCUMENTS

| | | | |
|---|---|---|---|
| 3,225,052 | 12/1965 | Jan Janssen | 546/199 |
| 3,255,196 | 6/1966 | Debarre et al. | 546/216 |
| 3,311,624 | 3/1967 | Ohnacker et al. | 544/129 |
| 3,632,767 | 1/1972 | Gray et al. | 514/330 |

(List continued on next page.)

FOREIGN PATENT DOCUMENTS

| | | |
|---|---|---|
| 43438/85 | 6/1985 | Australia. |
| 860701 | 5/1978 | Belgium. |
| 696999 | 11/1964 | Canada. |
| 149088 | 7/1985 | European Pat. Off.. |
| 0235463 | 9/1987 | European Pat. Off.. |
| 235463 | 9/1987 | European Pat. Off.. |
| 0308328 | 3/1989 | European Pat. Off.. |
| 337136 | 10/1989 | European Pat. Off.. |
| 0351282 | 1/1990 | European Pat. Off.. |
| 0398578 | 11/1990 | European Pat. Off.. |
| 0481853 | 4/1991 | European Pat. Off.. |
| 0445701 | 9/1991 | European Pat. Off.. |
| 0449186 | 10/1991 | European Pat. Off.. |
| 488959 | 6/1992 | European Pat. Off.. |
| 0524846 | 1/1993 | European Pat. Off.. |
| 572952 | 12/1993 | European Pat. Off.. |
| 0648744 | 4/1995 | European Pat. Off.. |
| 649838 | 4/1995 | European Pat. Off.. |
| 709384 | 10/1995 | European Pat. Off.. |
| 2681319 | 3/1993 | France. |
| 2939292 | 4/1981 | Germany. |
| 3703435 | 8/1988 | Germany. |
| 4410822 | 9/1995 | Germany. |
| 61-115068 | 6/1986 | Japan. |
| 61-227565 | 10/1986 | Japan. |
| 4-36279 | 2/1992 | Japan. |
| 04217945 | 8/1992 | Japan. |
| 4-312572 | 11/1992 | Japan. |
| 1055548 | 1/1967 | United Kingdom. |
| 2056435 | 3/1981 | United Kingdom. |
| WO 91/06297 | 5/1971 | WIPO. |
| WO 88/02365 | 4/1988 | WIPO. |
| WO 91/17156 | 11/1991 | WIPO. |
| WO 92/02502 | 2/1992 | WIPO. |
| WO 92/07831 | 10/1992 | WIPO. |
| WO 92/18127 | 10/1992 | WIPO. |
| WO 93/00313 | 1/1993 | WIPO. |
| WO 93/15052 | 2/1993 | WIPO. |
| WO 93/11107 | 6/1993 | WIPO. |
| WO 93/02052 | 8/1993 | WIPO. |
| WO 94/10166 | 5/1994 | WIPO. |
| WO 94/13275 | 6/1994 | WIPO. |
| WO 94/18172 | 8/1994 | WIPO. |

OTHER PUBLICATIONS

Sam "phenylalkylamine" CA 68:104922, 1967.
Dixon "Piperidine derivatives" CA 100:174627, 1984.
Sugaya et al. "preparation of optically active . . . " CA 117:69745, 1992.
Brown "Preparation of phenoxyalkylpiperidines . . . " CA 120:106766, 1993.
Saxena et al. "Synthesis and QSAR . . . " CA 120:244964, 1993.
Ding et al. "Synthesis of the racemate . . . " CA 122:31279, 1994.
Glennon et al. "Sigma receptor ligands . . . " CA 122:205210, 1995.
Loew "Structure–activity studies of morphine . . . " CA 116:98898, 1991.
Sundaram "NMDA receptors in the intermediolatedral . . . " Medline 91308941, 1991.
J.H. Arundel, et al., J. Med. Chem. 9, 555–558 (1966).
A.K. Saxena, et al., Chem. Abstracts, vol. 120, No. 19, 120:244964e (1994).
B. Costall, et al., Chem. Abstracts, vol. 91, No. 21, 91:168329s (1979).

(List continued on next page.)

*Primary Examiner*—Ceila Chang
*Attorney, Agent, or Firm*—Fitzpatrick, Cella, Harper & Scinto

[57] ABSTRACT

Novel 2-substituted piperidine analogs, pharmaceutical compositions containing the same and the method of using 2-substituted piperidine analogs as selectively active antagonists of N-methyl-D-aspartate (NMDA) receptor subtypes for treating conditions such as stroke, cerebral ischemia, central nervous system trauma, hypoglycemia, anxiety, convulsions, amioglycoside antibiotics-induced hearing loss, migraine headaches, chronic pain, glaucoma, CMV retinitis, psychosis, urinary incontinence, opioid tolerance or withdrawal, or neurodegenerative disorders, such as lathyrism, Alzheimer's Disease, Parkinsonism and Huntington's Disease are described.

13 Claims, No Drawings

U.S. PATENT DOCUMENTS

| | | | |
|---|---|---|---|
| 3,686,187 | 8/1972 | Cole et al. | 546/223 |
| 4,146,630 | 3/1979 | Kampe et al. | 546/199 |
| 4,482,560 | 11/1984 | Banno et al. | 514/312 |
| 4,567,186 | 1/1986 | Lesher et al. | 514/300 |
| 4,567,187 | 1/1986 | Banno et al. | 514/312 |
| 4,577,020 | 3/1986 | Gall | 544/366 |
| 4,643,995 | 2/1987 | Engel et al. | 514/210 |
| 4,876,257 | 10/1989 | Hajos | 514/253 |
| 4,902,695 | 2/1990 | Ornstein | 514/307 |
| 4,942,169 | 7/1990 | Sagimoto et al. | 514/318 |
| 5,011,834 | 4/1991 | Weber et al. | 514/212 |
| 5,036,077 | 7/1991 | Van Broeck et al. | 514/317 |
| 5,169,855 | 12/1992 | Cain et al. | 514/319 |
| 5,192,751 | 3/1993 | Thor | 514/82 |
| 5,192,799 | 3/1993 | Tomino et al. | 514/469 |
| 5,202,346 | 4/1993 | Butera et al. | 514/326 |
| 5,273,977 | 12/1993 | Glase et al. | 514/277 |
| 5,302,602 | 4/1994 | Oshima et al. | 514/325 |
| 5,352,683 | 10/1994 | Mayer et al. | 514/589 |
| 5,466,698 | 11/1995 | Glase et al. | 514/318 |
| 5,620,988 | 4/1997 | Glase et al. | 514/307 |

OTHER PUBLICATIONS

M. Lauritzen, Acta. Neurol. Scand. 76 (Suppl. 113), 4–40 (1987).
De Lean et al., Am. J. Physiol. 235, E97–102 (1978).
W.U. Schmidt, et al., Amino Acids 1, 225–237 (1991).
T. Klockgether, L. Turski, Ann. Neurol. 34, 585–593 (1993).
Annu. Rev. Neurosci. 17, 31–108 (1994).
R.W. Gifford, et al., Arch. Intern. Med. 153, 154–183, (1993).
Harper and Powers, Biochemistry 24, 7200–7213 (1985).
Sugihara et al., Biochem. Biophys Res. Commun. 185, 826–832 (1992).
C.F. Bigge, Biochem. Pharmacol. 45, 1547–1561 (1993).
M. Lauritzen et al., Brian Res. 475, 317–327 (1988).
J.E. Haley, et al., Brain Res. 518, 218–226 (1990).
Shaw et al., Brain Research 539, 164–168 (1991).
Marek et al., Brain Res. 547, 77–81 (1991).
Lutfy et al., Brain Res. 616, 83–88 (1993).
P.H. Hutson, et al., Br. J. Pharmacol. 103, 2037–2044 (1991).
L.J. Bristow, et al., Br. J. Pharmacol. 108, 1156–1163 (1993).
Chemical Abstracts, vol. 94, No. 15, 94:121260j.
Chemical Abstracts, vol. 115, No. 23, 115:247459b.
D. Lonsdale, Dev. Pharmacol. Ther. 4, 28–36 (1982).
B.V. Clineschmidt et al., Drug Dev. Res. 2, 147–163 (1982).
Rojas et al. Drug Dev. Res. 29, 222–226 (1993).
J.H. Kehne et al., Eur. J. Pharmacol. 193, 283–292 (1991).
J. Winslow et al., Eur. J. Pharmacol. 190, 11–21 (1990).
R. Dunn et al., Eur. J. Pharmacol. 214, 207–214 (1992).
E.W. Anthony, Eur. J. Pharmacol. 250, 317–324 (1993).
Ikeda et al., FEBS Lett. 313, 34–38 (1992).
D.L. Comins et al., J. Am. Chem. Soc. 116, 4719–4728 (1994).
DeGroat et al., J. Auton. Nerv. Sys. 3, 135–160 (1981).
Ishii et al., J. Biol. Chem. 288, 2836–2843 (1993).
Decker et al., J. Immunol. Methods 15, 61–69 (1988).
Harbert et al., J. Med. Chem. 23, 635–643 (1980).
Abou–Gharbia et al., J. Med. Chem. 30, 1818–1823 (1987).
N. Iwasaki et al., J. Med. Chem. 38, 496–507 (1995).
Kerrigan et al., J. Med. Chem. 38, 544–552 (1995).
Cook et al., J. Med. Chem. 38, 753–763 (1995).
J.N. Dumont, J. Morphol. 136, 153–179 (1972).
P.T. Francis, N.R. Sims, A.W. Procter, D.M. Bowen, J. Neurochem. 60(5), 1589–1604 (1993).
W. Danysz et al., J. Neural Trans. 7, 155–166, (1994).
A.A.P.J. Leaó, Neurophysiol. 7, 359–390 (1944).
D.W. Choi et al., J. Neuroscience 7, 357–368 (1987).
S.R. Skilling et al, J. Neuro Sci. 10, 1309–1318 (1990).
D.L. Comins et al., J. Org. Chem. 55, 2574–2576 (1990).
Way et al., J. Pharmacol. Exp. Ther. 167, 1–8 (1969).
Huidobro et al., J. Pharmacol. Exp. Ther. 198, 318–329 (1976).
L.D. Snell et al., J. Pharmacol. Exp. Ther. 235, 50–57 (1985).
Lutfy et al., J. Pharmacol. Exp. Ther. 256, 575–580 (1991).
Tiseo et al., J. Pharmacol. Exp. Ther. 264, 1090–1096 (1993).
Miledi and Parker, J. Physiol. 357, 173–183 (1984).
Miledi and Woodward, J. Physiol. 416, 601–621 (1989).
Landon and Robbins, Methods in Enzymology 124, 412–425 (1986).
Woodward et al., Mol. Pharmacol. 41, 89–103 (1992).
Curtis et al., Nature 191, 1010–1011 (1961).
Moriyoshi, et al. Nature 354, 31–37 (1991).
Kutsuwada et al., Nature 358, 36–41 (1992).
Basile, et al., Nature Medicine, 2, 1338–1343, (1996).
Herman et al., Neuropsychopharmacology 13, 269–293 (1995).
Dickenson and Aydar, Neuroscience Lett. 121, 263–266 (1991).
Vera and Nadelhaft, Neuroscience Lett. 134, 135–138 (1991).
S.A. Lipton, P.A. Rosenberg, New Eng. J. Med. 330 (9), 613–622 (1994).
Org. Reactions 6, 151–206 (1951).
Dubuisson and Dennis, Pain 4, 161–174 (1977).
M. Fieser, L.F. Fieser, Reagents for Organic Synthesis 6, 183 (1977).
Kornetsky et al., Science 162, 1011–1012 (1968).
Sansalla et al., Science 243, 398–400 (1989).
Trujillo et al., Science 251, 85–87 (1991).
Monyer et al., Science 256, 1217–1221 (1992).
R.A. Sharma, W. Korytnyk, Tetrahedron Lett. 573–576 (1977).
D.L. Comins, et al., Tetrahedron Lett. 29, 773–776 (1988).
D.L. Comins, et al., Tetrahedron Lett. 32, 5697–5700 (1991).
S. Lipton, TINS 16(12), 527–532 (1993).
Carlsson et al., Trends Neurosci. 13, 272–276 (1990).
Tepley et al., *Biomagnetism*, eds. S. Williamson, L. Kaufmann, pp. 327–330, Plenum Press, New York (1990).
S.A. Glase et al., J. Med. Chem. 39, 3179–3187 (1996).
B.L. Chenard et al., J. Med. Chem. 34, 3085–3090 (1991).

2-SUBSTITUTED PIPERIDINE ANALOGS AND THEIR USE AS SUBTYPE-SELECTIVE NMDA RECEPTOR ANTAGONISTS

This application is 371 of PCT/W96/20767 filed Dec. 20, 1996 which claimed priority benefit of provisional application Ser. No. 60/009,182 filed Dec. 22, 1995.

BACKGROUND OF THE INVENTION

1. Field of the Invention

This invention is related to 2-substituted piperidine analogs. The analogs are selectively active as antagonists of N-methyl-D-aspartate (NMDA) receptor subtypes. The invention is also directed to the use of 2-substituted piperidine analogs as neuroprotective agents for treating conditions such as stroke, cerebral ischemia, central nervous system trauma, hypoglycemia, anxiety, convulsions, aminoglycoside antibiotics-induced hearing loss, migraine headaches, chronic pain, glaucoma, CMV retinitis, psychosis, urinary incontinence, opioid tolerance or withdrawal, or neuro-degenerative disorders such as lathyrism, Alzheimer's Disease, Parkinsonism and Huntington's Disease.

2. Related Background Art

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-Aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Various classes of substituted piperidine analogs are known. For example, U.S. Pat. No. 5,036,077 generically discloses piperidine derivatives described by the formula:

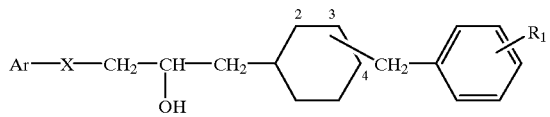

wherein Ar represents a phenyl group substituted by $R_2$, $R_3$ and $R_4$ or a naphth-1-yl or naphth-2-yl group, substituted or unsubstituted by 1 or 2 halogen atoms; X represents an oxygen atom or sulfur atom; $R_1$ represents H or a halogen atom; $R_2$ represents a halogen atom, a trifluoromethyl group, a phenyl group which is unsubstituted or substituted by 1 to 3 halogen atoms, a phenoxy group which is unsubstituted or substituted by 1 to 3 halogen atoms, or a $C_1$–$C_4$ alkyl group and the benzyl group substitutes the piperidine radical in the 2, 3 or 4 position. This reference does not exemplify 2-substituted piperidines. The piperidines are said to be useful as antimicrobial agents, but there is no disclosure or suggestion of treating disorders responsive to selective NMDA receptor subtype antagonists.

Canadian Patent No. 696,999 is directed to N-(alkylene) aryl-2-substituted piperidines useful as vasodilators which are described by the formula:

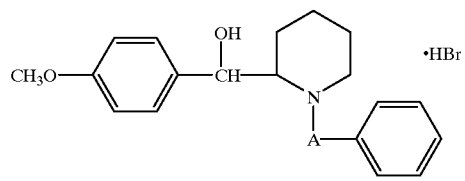

wherein A is an alkylene group having 2 to 3 carbon atoms. There is no mention of using the compounds of this reference as NMDA receptor antagonists or treating disorders responsive thereto.

PCT International Publication Number WO 93/15052 generically describes compounds that are said to be calcium channel antagonists represented by the formula:

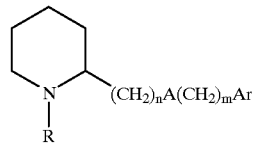

and the salts thereof, wherein R is $C_{1-8}$ alkyl(phenyl)p, $C_{2-8}$ alkenyl(phenyl)p, $C_{2-8}$ alkynyl(phenyl)p, $C_{3-8}$ cycloalkyl or $C_{1-8}$ alkyl $C_{3-8}$ cycloalkyl;

p is 0 to 2;
n is 0 to 6;
m is 0 to 6;
A is a bond, —CH=CH—, —C≡C—, oxygen, sulphur or $NR^1$;
$R^1$ is hydrogen, $C_{1-8}$ alkyl or phenyl $C_{1-4}$ alkyl; and
Ar is aryl or heteroaryl, each of which may be optionally substituted. 2-[2-(3,4-Dichlorophenoxy)ethyl]-1-cinnamylpiperidine oxalate hemihydrate and 4-[2-(2-Dibenzofuranyloxy)ethyl]-1-cinnamylpiperidine oxalate are exemplified. The compounds of this reference are said to be useful for treating anoxia, ischaemia, such as stroke, migraine, epilepsy, traumatic head injury, AIDS-related dementia, neurodegenerative diseases and drug addiction withdrawal. This reference does not disclose or suggest NMDA receptor activity, let alone selective NMDA receptor subtype antagonism.

European Patent Application No. 235,463 generically discloses calcium antagonists represented by the formula

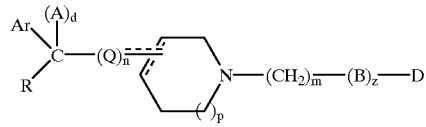

wherein;

p is zero, one or two;

A is hydrogen, —O—$R^1$, —C≡N, —$\overset{O}{\overset{\|}{C}}$N$R^1R^2$,

—$\overset{O}{\overset{\|}{C}}$—$R^1$, —$\overset{O}{\overset{\|}{C}}$—O—$R^1$, —O—$\overset{O}{\overset{\|}{C}}$—$R^1$, -continued

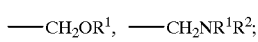

m is zero to six inclusive;

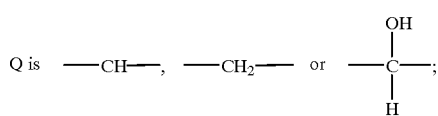

d and n are selected from zero or one and the dotted lines represent double bonds which may form consistent with the valence of carbon;

Ar, D and R are selected from the group consisting of

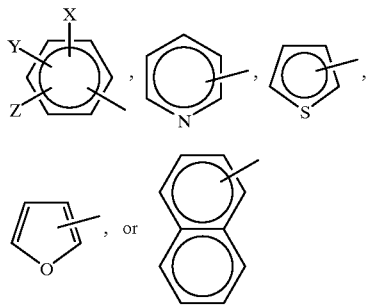

and in addition, R may have the values:

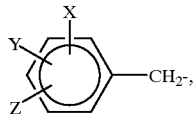

cycloalkyl or loweralkyl, and

D may have additionally the values:

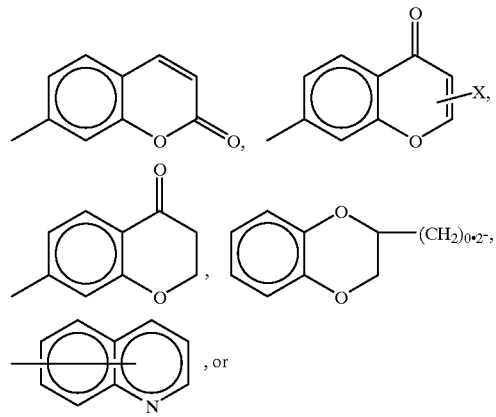

Ar (CH$_2$)$_{1-4}$,

X, Y and Z are selected from the group consisting of hydrogen, lower alkyl, halogen,

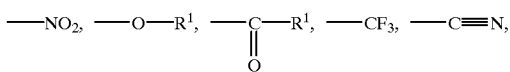
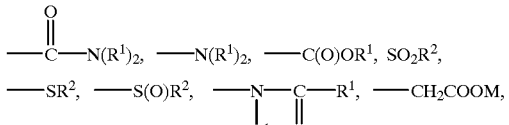
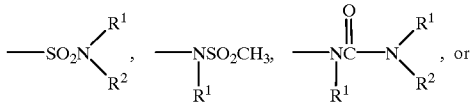
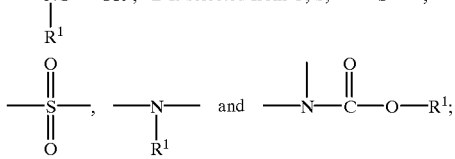

z is one or zero with the proviso that z cannot be zero at the same time n is zero when one of the following occurs at the same time that D is phenyl or substituted phenyl: (A)$_d$ is hydrogen, (A)$_d$ is cyano, (A)$_d$ is aminocarbonyl, or a double bond forms between the α carbon and a carbon of the central heterocyclic amine-ring; R$^1$ is selected from hydrogen, loweralkyl, phenyl and phenylloweralkyl; R$^2$ is selected from loweralkyl, phenyl and phenylloweralkyl; M is a pharmaceutically acceptable metal ion and the pharmaceutically acceptable salts thereof, including acid addition salts, quaternary salts, and hydrates and alcoholates thereof. This reference discloses that such compounds may be useful as coronary vasodilators, antihypertensives, antiarrhythmic, antiallergy, antihistamic and antisecretory agents. No compounds substituted at the 2 position of the piperidine ring are exemplified nor is there any disclosure or suggestions of NMDA antagonistic activity.

U.S. Pat. No. 5,192,799 generically disclosed amines described by the formula:

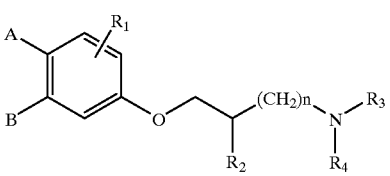

wherein R$_3$–R$_4$ can be taken together to form 4- to 8-membered ring and substituted by aryl, benzyl and heteroaryl. No 2-benzylpiperidine was exemplified in this reference. The compounds are said to be useful for the treatment and prevention of heart diseases. But there is no disclosure or suggestion of treating disorders responsive to selective NMDA receptor subtype antagonists.

European patent application No. 649838 generically disclosed cyclized amines described by the formula:

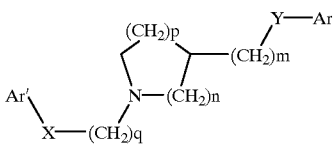

wherein the nitrogen heterocycles can be 3–8 member rings and substituted in the 2–4 positions. Ar and Ar' are opt. mono or disubstituted phenyl. No. 2-benzylpiperidine was exemplified in this reference. The compounds are said to be useful to treat arrhythmia and tachycardia. But there is no disclosure or suggestion of treating disorders responsive to selective NMDA receptor subtype antagonists.

Japanese patent application No. 04217945 disclosed amines described by the formula:

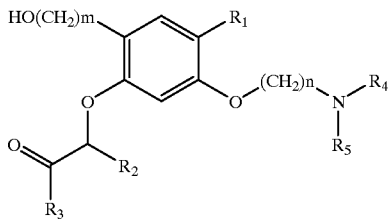

wherein $R_4$–$R_5$ can be taken together to form 5- to 8-membered ring and substituted by benzyl and phenyl. The compounds are said to be useful as antiulcer agents. But there is no disclosure or suggestion of treating disorders responsive to selective NMDA receptor subtype antagonists.

U.S. Pat. No. 5,169,855 generically discloses disubstituted piperidine ether derivatives for use as antipsychotic agents selective for sigma receptors. Similarly, PCT International Publication No. WO 92/18127 and PCT International Publication No. WO 91/06297 generically disclose N-phthalimidoalkyl piperidines which are useful as antipsychotic agents and which are selective for sigma receptors. However, 2-substituted piperidines are not exemplified by any of these references and there is no mention of NMDA receptor activity.

Numerous references have disclosed piperidine derivatives substituted at the 4 and 3 position for use in a variety of treatments. Such references include, for example, U.S. Pat. No. 3,255,196 (3 and 4-substituted piperidines that are active antitussives and possess analgesic, antiemetic and local anaesthetic properties); U.S. Pat. No. 5,202,346 (4-substituted piperidines that are Class III antiarrhythmic agents); PCT International Publication No. WO 92/02502 (3 and 4-substituted piperidines which are calcium channel blockers expected to be useful in the treatment of anoxia, ischemia including stroke, migraine, epilepsy, traumatic head injury, AIDS-related dementia, neurodegenerative diseases and drug addiction); PCT International Publication No. WO 88/02365 (3 and 4-substituted piperidines that may be useful for treatment of mental disorders accompanying cerebrovascular disease); BE 860701 (4-substituted piperidines for use as vasodilators and β-adrenergic inhibitors); FR 2681319 (4-substituted piperidines for use as neuroprotectors and anticonvulsants); and DE 2939292 (4-substituted piperidines for use as antiallergenic and antiinflammatory agents). None of these references discloses or suggest 2-substituted piperidine analogs or their use as selective NMDA receptor subtype antagonists.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

Expression cloning of the first NMDA receptor subunit, NMDAR1 (NR1) in Nakanishi's lab in 1991 provided an initial view of the molecular structure of the NMDA receptor [Nature 354, 31–37 (1991)]. There are several other structurally related subunits (NMDAR2A through NMDAR2D) that join NR1 in heteromeric assemblies to form the functional ion channel complex of the receptor [Annu. Rev. Neurosci. 17, 31–108 (1994)]. The molecular heterogeneity of NMDA receptors implies a future potential for agents with subtype selective pharmacology.

Many of the properties of native NMDA receptors are seen in recombinant homomeric NR1 receptors. These properties are altered by the NR2 subunits. Recombinant NMDA receptors expressed in Xenopus oocytes have been studied by voltage-clamp recording, as has developmental and regional expression of the mRNAs encoding NMDA receptor subunits. Electrophysiological assays were utilized to characterize the actions of compounds at NMDA receptors expressed in Xenopus oocytes. The compounds were assayed at four subunit combinations of cloned rat NMDA receptors, corresponding to four putative NMDA receptor subtypes [Moriyoshi, et al. Nature 1991, 354, 31–37; Monyer et al, Science 1992, 256, 1217–1221; Kutsuwada et al, Nature 1992, 358, 36–41; Sugihara et al, Biochem. Biophys Res. Commun. 1992, 185, 826–832].

An object of this invention is to provide novel 2-substituted piperidine analogs which function as subtype-selective NMDA receptor antagonists.

A further object of this invention is to provide a pharmaceutical composition containing an effective amount of the 2-substituted piperidine analogs to treat cerebrovascular disorders responsive to the selective blockade of NMDA receptor subtypes.

Another object of this invention is to provide a method of treating disorders responsive to the subtype-selective NMDA receptor antagonists in an animal by administering a pharmaceutically effective amount of 2-substituted piperidine analogs.

SUMMARY OF THE INVENTION

This invention relates to novel 2-substituted piperidine analogs represented by the formula (I):

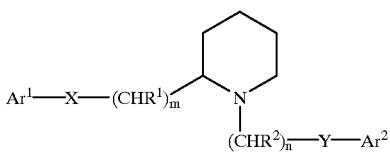

(I)

or a pharmaceutically acceptable salt thereof wherein
  $Ar^1$ and $Ar^2$ are independently aryl or a heteroaryl group, either of which may be independently substituted by hydrogen, hydroxy, alkyl, a halogenated alkyl group, halogen, nitro, aryl, aralkyl, amino, a lower alkyl amino group or a lower alkoxy group;
  each $R^1$ is independently hydrogen, alkyl or hydroxy;
  each $R^2$ is independently hydrogen, alkyl or hydroxy;
  X is —$CH_2$—, O, S or $NR^3$, wherein $R^3$ is hydrogen or a lower alkyl group having 1 to 6 carbon atoms;
  Y is —$CH_2$—, —CH=CH—, —C≡C—, O, S or $NR^3$;
  m is 0, 1 or 2; and
  n is 0, 1, 2, 3, 4 or 5,
  provided that when m is 0 and X is —$CH_2$—, or m is 1, $R^1$ is H and X is —$CH_2$— that either Y is not —$CH_2$— or at least one of $R^2$ is not hydrogen and further provided that when Y is —C≡C— then X is not O.

The compounds of the present invention may exist as optical isomers and the inventive compounds include both the racemic mixtures of such optical isomers as well as the individual entantiomers.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate. Alternatively, pharmaceutically acceptable inorganic and organic base addition salts may be used such as sodium hydroxide, potassium hydroxide, lithium hydroxide and the like.

Halogen is fluorine, chlorine, bromine, or iodine; fluorine, chlorine, and bromine are preferred groups.

Alkyl means a straight or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Aryl means a monocyclic or bicyclic carbocyclic aromatic ring system which can be substituted or unsubstituted, for example, but not limited to phenyl, naphthyl or the like.

Heteroaryl means a monocyclic or bicyclic carbocyclic aromatic ring system substituted by one or more hetero atoms, which can be the same or different, and includes, for example, thienyl, benzo[b]thienyl, naphtho [2,3[b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl groups, quinoxalinyl, 2,3-dioxoquinoxalinyl, benzimidazolyl, 2-oxobenzimdazolyl and 2-oxindolyl groups.

Aralkyl means any of the alkyl groups defined herein substituted by any of the aryl groups as defined herein.

Halogenated alkyl means any of the alkyl groups defined herein substituted by one or more of the halogen groups defined herein, including but not limited to a trifluoromethyl group.

Lower alkyl amino means any of the alkyl groups defined herein substituted by an amino group.

Lower alkoxy means an alkoxy group containing an alkyl group as defined herein.

The instant invention is also related to a pharmaceutical composition containing the compound defined by formula I in an amount effective to treat cerebrovascular disorders responsive to the selective blockade of NMDA receptor subtypes and a pharmaceutically acceptable carrier. Exemplary disorders responsive to such treatment include cerebral ischemia caused by cerebral trauma, stroke, hypoglycemia, heart attack, and surgery; anxiety; psychosis; schizophrenia; glaucoma; CMV retinitis, urinary incontinence; opioid tolerance of withdrawal; and chronic neurodegenerative disorders such as Huntington's disease, ALS, Parkinsonism and Alzheimer's disease. The pharmaceutical composition of this invention may also be employed as an analgesic or for the treatment of epilepsy or migraine headaches.

The invention further relates to a method for treating disorders responsive to the selective blockade of N-methyl-D-aspartate receptor subtypes in an animal suffering thereof which comprises administering in unit dosage form at least one compound represented by the formula:

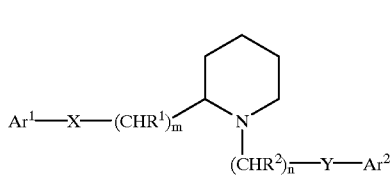

(I)

or a pharmaceutically acceptable salt thereof wherein
  $Ar^1$ and $Ar^2$ are independently aryl or a heteroaryl group, either of which may be independently-substituted by hydrogen, hydroxy, alkyl, a halogenated alkyl group, halogen, nitro, aryl, aralkyl, amino, a lower alkyl amino group or a lower alkoxy group;
  each $R^1$ is independently hydrogen, alkyl or hydroxy;
  each $R^2$ is independently hydrogen, alkyl or hydroxy;
  X is —$CH_2$—, O, S or $NR^3$, wherein $R^3$ is hydrogen or a lower alkyl group having 1 to 6 carbon atoms;
  Y is —$CH_2$—, —CH=CH—, —C≡C—, O, S or $NR^3$;
  m is 0, 1 or 2; and
  n is 0, 1, 2, 3, 4 or 5.

DETAILED DESCRIPTION OF THE INVENTION

The novel 2-substituted piperidine analogs of this invention are represented by previously defined formula (I).

Preferred embodiments of the novel 2-substituted piperidine analogs of this invention are represented by formulae (III–VI). In particular, one embodiment is represented by formula (III) as follows:

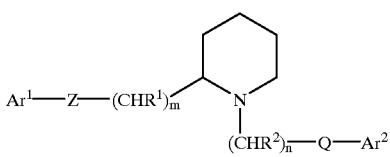

(III)

or a pharmaceutically acceptable salt thereof wherein $Ar^1$ and $Ar^2$ are independently aryl or a heteroaryl group, either of which may be independently substituted by hydrogen, hydroxy, alkyl, a halogenated alkyl group, halogen, nitro, aryl, aralkyl, amino, a lower alkyl amino group or a lower alkoxy group;

each $R^1$ is independently hydrogen, alkyl or hydroxy;
each $R^2$ is independently hydrogen, alkyl or hydroxy;
Q is —C=C— or —C≡C—;
Z is —CH$_2$—, O, S or $NR^3$;
m is 0, 1 or 2; and
n is 0, 1, 2, 3, 4 or 5, provided that when Q is —C=C— then Z is not O.

Two additional embodiments of the novel 2-substituted piperidine analogs of this invention are represented by formulae (IV–V) as follows:

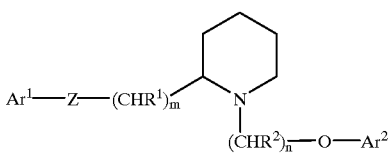

(IV)

or a pharmaceutically acceptable salt thereof, or

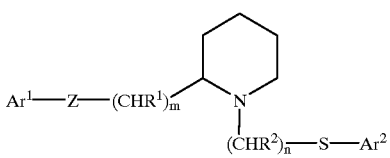

(V)

or a pharmaceutically acceptable salt thereof, wherein $Ar^1$, $Ar^2$, $R^1$, $R^2$, Z, m and n are the same as previously defined.

Yet another embodiment of the novel compounds of this invention is represented by the formula (VI):

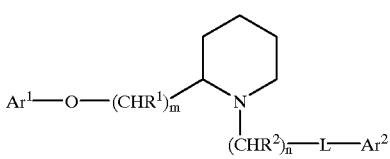

(VI)

or a pharmaceutically acceptable salt thereof, wherein $Ar^1$, $Ar^2$, $R^1$, $R^2$, m and n are the same as previously defined and L is —CH$_2$—, O, S or $NR^3$.

Exemplary preferred compounds of formula I include, without limitation:

*2-Benzyl-1-(2-phenoxy)ethylpiperidine;
*2-Benzyl-1-(2-(4-trifluoromethyl)phenoxy)ethylpiperidine;
**2-Benzyl-1-(2-(3-amino)phenoxy)ethylpiperidine
**2-(4-chlorophenyl)methyl-1-(2-(3-amino)phenoxy)ethylpiperidine;
**2-Benzyl-1-(3-phenoxy)propylpiperidine;
*2-Benzyl-1-(3-(4-trifluoromethyl)phenoxy)propylpiperidine;
*2-(4-chlorophenyl)methyl-1-(3-(3-amino)phenoxy)propylpiperidine;
**2-Benzyl-1-(4-phenoxy)butylpiperidine;
*2-Benzyl-1-(4-(3-trifluoromethyl)phenoxy)butylpiperidine;
*2-Benzyl-1-(4-(3-amino)phenoxy)butylpiperidine;
2-Benzyl-1-(4-(2-trifluoromethy)phenoxy)butylpiperidine;
**2-Benzyl-1-(4-(4-trifluoromethyl)phenoxy)butylpiperidine;
**2-Benzyl-1-(4-(3-fluoro)phenoxy)butylpiperidine;
2-Benzyl-1-(3-(3-phenyl)propynyl)piperidine;
*2-Benzyl-1-[3-(4-trifluoromethyl)phenyl)propynyl]piperidine;
*2-(4-chlorophenyl)methyl-1-[4-(3-amino)phenyl)butynyl]piperidine;
**2-Benzyl-1-[2-hydroxy-3-(2-methyl)phenoxy]propylpiperidine;
**2-[(2-Ethoxy)phenoxy]methyl-1-(3-phenoxy)propylpiperidine;
*2-[(2-Ethoxy)phenoxy]methyl-1-(3-(3-amino)phenoxy)propylpiperidine;
*2-[(2-Ethoxy)phenoxy]methyl-1-(3-(4-trifluoromethyl)phenoxy)propylpiperidine;
*2-[(2-Ethoxy)phenoxy]methyl-1-(3-(4-trifluoromethyl)phenyl)propylpiperidine;
**2-Benzyl-1-(5-phenoxypentyl)piperidine;
**2-Benzyl-1-(2-(4-nitrophenoxy)ethyl)piperidine;
**1-(2-(4-Aminophenoxy)ethyl)-2-benzylpiperidine;
**2-Benzyl-1-(2-(4-amino-3-nitrophenoxy)ethyl)piperidine;
**2-Benzyl-1-(2-(2-oxobenzimidazol-5-oxy)ethyl)piperidine;
**2-(4-Chlorobenzyl)-1-(2-(4-fluorophenoxy)ethyl)piperidine;
**2-(4-Chlorobenzyl)-1-(2-(4-hydroxyphenoxy)ethyl)piperidine;
**2-Benzyl-1-(2-(4-hydroxyphenoxy)ethyl)piperidine;
**2-Benzyl-1-(2-(4-hydroxyphenoxy)propyl)piperidine;
**2-Benzyl-1-(2-(4-hydroxyphenoxy)butyl)piperidine; and
2-[(4-chloro)phenoxy]methyl-1-(3-phenoxy)propylpiperidine.

Of the above-listed exemplary compounds, the more preferred compounds are designated * and the most preferred are designated **.

The compounds of this invention may be prepared by methods known to one of ordinary skill in the art or readily adaptable from such known methods without undue experimentation. Starting materials employed for the preparation of the inventive compounds are readily available or the preparation thereof is well within the knowledge and ability of one of ordinary skill.

The invention is also directed to a method for treating disorders responsive to the selective blockade of NMDA receptor subtypes in animals suffering thereof. Particular preferred embodiments of the 2-substituted piperidine analogs for use in the method of this invention are represented by previously defined formulae (III–VI) as well as by the compound represented by formula (II):

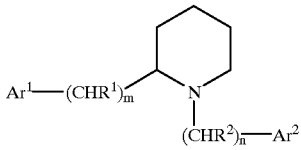

(II)

or a pharmaceutically acceptable salt thereof, wherein $Ar^1$, $Ar^2$, $R^1$, $R^2$, m and n are the same as previously defined.

Exemplary preferred compounds that may be employed in the method of this invention include, without limitation:

*1,2-Dibenzylpiperidine;
2-Benzyl-1-(4-fluorophenyl)methylpiperidine;
2-Benzyl-1-(4-trifluoromethylphenyl)methylpiperidine;
*2-(4-chlorophenyl)methyl-1-(4-trifluoromethylphenyl)methylpiperidine;
2-Benzyl-1-(2-phenyl)ethylpiperidine;
2-Benzyl-1-(2-(3-fluoro)phenyl)ethylpiperidine;
*2-Benzyl-1-(2-(4-trifluoromethyl)phenyl)ethylpiperidine;
**2-(4-chlorophenyl)methyl-1-(2-(4-fluoro)phenyl)ethylpiperidine;
**2-(4-chlorophenyl)methyl-1-(2-(3-amino)phenyl)ethylpiperidine;
**2-Benzyl-1-(3-phenyl)propylpiperidine;
*2-Benzyl-1-(3-(4-trifluoromethyl)phenyl)propylpiperidine;
**2-(4-chlorophenyl)methyl-1-(3-(3-trifluoromethyl)phenyl)propylpiperidine;
**2-Benzyl-1-(4-phenyl)butylpiperidine;
*2-Benzyl-1-(4-(3-trifluoromethyl)phenyl)butylpiperidine;
**2-(3,4-dichlorophenyl)methyl-1-(4-(4-trifluoromethyl)phenyl)butylpiperidine;
*2-Benzyl-1-(2-phenoxy)ethylpiperidine;
*2-Benzyl-1-(2-(4-trifluoromethyl)phenoxy)ethylpiperidine;
**2-Benzyl-1-(2-(3-amino)phenoxy)ethylpiperidine
**2-(4-chlorophenyl)methyl-1-(2-(3-amino)phenoxy)ethylpiperidine;
**2-Benzyl-1-(3-phenoxy)propylpiperidine;
*2-Benzyl-1-(3-(4-trifluoromethyl)phenoxy)propylpiperidine;
*2-(4-chlorophenyl)methyl-1-(3-(3-amino)phenoxy)propylpiperidine;
**2-Benzyl-1-(4-phenoxy)butylpiperidine;
*2-Benzyl-1-(4-(3-trifluoromethyl)phenoxy)butylpiperidine;
*2-Benzyl-1-(4-(3-amino)phenoxy)butylpiperidine;
2-Benzyl-1-(4-(2-trifluoromethy)phenoxy)butylpiperidine;
**2-Benzyl-1-(4-(4-trifluoromethyl)phenoxy)butylpiperidine;
**2-Benzyl-1-(4-(3-fluoro)phenoxy)butylpiperidine;
2-Benzyl-1-(3-phenyl)propynyl)piperidine;
*2-Benzyl-1-[3-(4-trifluoromethyl)phenyl)propynyl]piperidine;
*2-(4-chlorophenyl)methyl-1-[4-(4-(3-amino)phenyl)butynyl]piperidine;
**2-Benzyl-1-[2-hydroxy-3-(2-methyl)phenoxy]propylpiperidine;
**2-[(2-Ethoxy)phenoxy]methyl-1-(3-phenoxy)propylpiperidine;
*2-[(2-Ethoxy)phenoxy]methyl-1-(3-(3-amino)phenoxy)propylpiperidine;
*2-[(2-Ethoxy)phenoxy]methyl-1-(3-(4-trifluoromethyl)phenoxy)propylpiperidine;
*2-[(2-Ethoxy)phenoxy]methyl-1-(3-(4-trifluoromethyl)phenyl)propylpiperidine;
**2-Benzyl-1-(5-phenoxypentyl)piperidine;
**2-Benzyl-1-(2-(4-nitrophenoxy)ethyl)piperidine;
**1-(2-(4-Aminophenoxy)ethyl)-2-benzylpiperidine;
**2-Benzyl-1-(2-(4-amino-3-nitrophenoxy)ethyl)piperidine;
**2-Benzyl-1-(2-(2-oxobenzimidazol-5-oxy)ethyl)piperidine;
**2-(4-Chlorobenzyl)-1-(2-(4-fluorophenoxy)ethyl)piperidine;
**2-(4-Chlorobenzyl)-1-(2-(4-hydroxyphenoxy)ethyl)piperidine;
**2-Benzyl-1-(2-(4-hydroxyphenoxy)ethyl)piperidine;
**2-Benzyl-1-(2-(4-hydroxyphenoxy)propyl)piperidine;
**2-Benzyl-1-(2-(4-hydroxyphenoxy) butyl)piperidine; and
2-[(4-chloro)phenoxy]methyl-1-(3-phenoxy)propylpiperidine.

Of the above-listed exemplary compounds, the more preferred compounds for use in the method of this invention are designated * and the most preferred are designated **.

The compounds of the present invention are useful in treating or preventing neuronal loss, neurodegenerative diseases and chronic pain. They are also useful as anticonvulsants and for inducing anesthesia, as well as for treating epilepsy and psychosis. The therapeutic and side effect profiles of selective NMDA receptor subtype antagonists and agonists should be markedly different from the more non-selective types of inhibitors. The subtype-selective analogs of the present invention are expected to exhibit little or no untoward side effects caused by non-selective binding with other receptors, particularly, the PCP and glutamate bindings sites associated with the NMDA receptor. In addition, selectivity for different NMDA receptor subtypes will reduce side effects such as sedation that are common to non-subtype-selective NMDA receptor antagonists. The compounds of the present invention are effective in treating or preventing the adverse consequences of the hyperactivity of the excitatory amino acids, e.g. those which are involved in the NMDA receptor system, by preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier which makes them particularly useful for treating or preventing conditions involving the central nervous system.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The subtype-selective NMDA receptor antagonists, agonists and modulators may be tested for in vivo anticonvulsant activity after intraperitoneal or intravenous injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the mouse. It is expected that such results will suggest that the subtype-selective NMDA receptor antagonists and agonists of the present invention do not show the PCP-like behavioral side effects that are common to NMDA channel blockers such as MK-801 and PCP or to competitive NMDA antagonists such as CGS 19755.

The subtype-selective NMDA receptor antagonists and agonists are also expected to show potent activity in vivo after intraperitoneal and intravenous injection suggesting that these compounds can penetrate the blood/brain barrier.

Elevated levels of glutamate has been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment of glaucoma. Preferably, the invention is directed to the treatment of patients which have primary open-angle glaucoma, chronic closed-angle glaucoma, pseudo doexfoliation, or other types of glaucoma or ocular hypertension. Preferably, the compound is administered over an extended period (e.g. at least six months and preferably at least one year), regardless of the changes in the patient's intraocular pressure over the period of administration. The compounds of the present invention are also useful in treating CMV retinitis, particularly in combination with antiviral agents. CMV afflicts the ganglion cell layer which may result in higher levels of glutamate. Thus, NMDA receptor antagonists could block retinitis by blocking the toxicity effect of high levels of glutamate.

Aminoglycoside antibiotics have been used successfully in the treatment of serious Gram-negative bacterial infections. However, prolonged treatment with these antibiotics will result in the destruction of sensory hearing cells of the inner ear and consequently, induce permanent loss of hearing. A recent study of Basile, et al. (Nature Medicine, 2: 1338–1344, 1996) indicated that aminoglycosides produce a polyamine-like enhancement of glutamate excitotoxicity through their interaction with the NMDA receptor. Thus, compounds of the present invention with NMDA receptor antagonist activity will be useful in preventing aminoglycoside antibiotics-induced hearing loss by antagonizing their interaction with the receptor.

The compounds of the present invention are useful in treating headaches, in particular, migraine headaches. During migraine attack, a sensory disturbance with unique changes of brain blood flow will result in the development of characteristic migraine auras. Since this unique phenomena has been replicated in animal experiments with cortical-spreading depression (CSD) of Leaó, A.A.P.J., Neurophysiol. 7:359–390 (1944), CSD is considered an important phenomena in the pathophysiology of migraine with aura (Tepley et al., In: Biomagnetism, eds. S. Williamson, L. Kaufmann, pp. 327–330, Plenum Press, New York (1990)). The CSD is associated with the propagation (2~6 mm/s) of transient changes in electrical activity which relate to the failure of ion homoestatis in the brain, efflux of excitatory amino acids from the neurons and increased energy metabolism (Lauritzen, M., Acta Neurol. Scand. 76 (Suppl. 113): 4–40 (1987)). It has been demonstrated that the initiation of CSD in a variety of animals, including humans, involved the release of glutamate and could be triggered by NMDA (Curtis et al., Nature 191:1010–1011 (1961); and Lauritzen et al., Brain Res. 475:317–327 (1988)). Subtype selective NMDA antagonists will be therapeutically useful for migraine headache because they can block CSD and subsequent pain and because of their expected low side effects, their ability to cross the blood brain barrier and their systemic bioavailability.

Bladder activity is controlled by parasympathetic preganglionic neurons in the sacral spinal cord (DeGroat et al., J. Auton. Nerv. Sys. 3:135–160(1981)). In humans, it has been shown that the highest density of NMDA receptors in the spinal cord are located at the sacral level, including those areas that putatively contain bladder parasympathetic preganglionic neurons (Shaw et al., Brain Research 539:164–168 (1991)). Because NMDA receptors are excitatory in nature, pharmacological blockade of these receptors would suppress bladder activity. It has been shown that the noncompetitive NMDA receptor antagonist MK801 increased the frequency of micturition in rat (Vera and Nadelhaft, Neuroscience Letters 134:135–138(1991)). In addition, competitive NMDA receptor antagonists have also been shown to produce a dose-dependent inhibition of bladder and of urethral sphincter activity (U.S. Pat. No. 5,192,751). Thus, it is anticipated that subtype-selective NMDA receptor antagonists will be effective in the treatment of urinary incontinence mediated by their modulation on the receptor channel activity.

Non-competitive NMDA receptor antagonist MK801 has been shown to be effective in a variety of animal models of anxiety which are highly predictive of human anxiety (Clineschmidt, B. V. et al., Drug Dev. Res. 2:147–163 (1982)). In addition, NMDA receptor glycine site antagonists are shown to be effective in the rat protentiated startle test (Anthony, E. W., Eur. J. Pharmacol. 250:317–324 (1993)) as well as several other animal anxiolytic models (Winslow, J. et al, Eur. J. Pharmacol. 190:11–22 (1990); Dunn, R. et al., Eur. J. Pharmacol. 214:207–214 (1992); and Kehne, J. H. et al, Eur. J. Pharmacol. 193:282–292 (1981)).

Glycine site antagonists, (+) HA-966 and 5,7-dichlorokynurenic acid were found to selectively antagonize d-amphetamine induced stimulation when injected into rat nucleus accumbens but not in striatum (Hutson, P. H. et al., Br. J. Pharmacol. 103:2037–2044 (1991)). Interestingly, (+) HA-966 was also found to block PCP and MK801-induced behavioral arousal (Bristow, L. J. et al., Br. J. Pharmacal, 108:1156–1163 (1993)). These findings suggest that a potential use of NMDA receptor channel modulators, but not channel blockers, as atypical neuroleptics.

It has been shown that in an animal model of Parkinson's disease—MPP+ or methamphetamine-induced damage to dopaminergic neurons—can be inhibited by NMDA receptor antagonists (Rojas et al., Drug Dev. Res. 29:222–226 (1993); and Sonsalla et al, Science 243;398–400 (1989)). In addition, NMDA receptor antagonists have been shown to inhibit haloperidol-induced catalepsy (Schmidt, W. J. et al., Amino Acids 1:225–237 (1991)), increase activity in rodents depleted of monoamines (Carlsson et al., Trends Neurosci. 13:272–276 (1990)) and increase ipsilateral rotation after unilateral substantia nigra lesion in rats (Snell, L. D. et al., J. Pharmacol. Exp. Ther. 235:50–57 (1985)). These are also experimental animal models of Parkinson's disease. In animal studies, the antiparkinsonian agent amantadine and memantine showed antiparkinsonian-like activity in animals at plasma levels leading to NMDA receptor antagonism (Danysz, W. et al., J. Neural Trans. 7:155–166, (1994)). Thus, it is possible that these antiparkinsonian agents act therapeutically through antagonism of an NMDA receptor. Therefore, the balance of NMDA receptor activity maybe important for the regulation of extrapyramidal function relating to the appearance of parkinsonian symptoms.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993); Herman et al., Neuropsychopharmacology 12:269–294 (1995).) Further, it has been reported that NMDA receptor antagonists are useful for inhibiting opioid tolerance and some of the symptoms of opioid withdrawal. Thus, the present invention is also directed to the administration of the compounds described herein to inhibit opiate tolerance and to treat or ameliorate the symptoms of opiate withdrawal by blocking the glycine co-agonist site associated with the NMDA receptor.

Thus, the present invention is directed to compounds having high affinity to a particular NMDA receptor subunit and low affinity to other sites such as dopamine and other catecholamine receptors, and σ sites. According to the present invention, those compounds having high binding to a particular NMDA subunit exhibit an $IC_{50}$ of about 100 μM or less in an NMDA subunit binding assay (see Table 1). Preferably, the compounds of the present invention exhibit a selective subunit $IC_{50}$ of 10 μM or less. Most preferably, the compounds of the present invention exhibit a selective subunit $IC_{50}$ of about 1.0 μM or less.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder and post traumatic stress disorders or for schizophrenia or other psychoses. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, to treat or prevent glaucoma or urinary incontinence, as well as for the treatment of Alzheimer's disease, amyotrophic lateral sclerosis, Huntington's disease, Parkinson's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain, migrane headache, to induce anesthesia, to treat or prevent opiate tolerance or to treat opiate withdrawal, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular selective NMDA receptor subtype antagonist or agonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular 2-substituted piperidine analog of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of NMDA subunit binding sites in vitro has been difficult because of the lack of selective drug ligands. Thus, the compounds of the present invention may be used to characterize the NMDA subunits and their distribution. Particularly preferred subtype-selective NMDA receptor antagonists and agonists of the present invention which may be used for this purpose are isotopically radiolabelled derivatives, e.g., where one or more of the atoms are replaced with $^3H$, $^{11}C$, $^{14}C$, $^{15}N$ or $^{18}F$.

Electrophysiological Assays at NMDA Receptor Subunits

Preparation of RNA. cDNA clones encoding the NR1A, NR2A, NR2B, NR2C and NR2D rat NMDA receptor subtypes were provided by Dr. P. H. Seeburg (see, Moriyoshi et al., *Nature* (Lond.) 354:31–37 (1991); Kutsuwada et al., *Nature* (Lond.) 358:36–41 (1992) Monyer et al., *Science* (Washington, D.C.) 256:1217–1221 (1992); Ikeda et al., *FEBS Lett.* 313:34–38 (1992); Ishii et al., *J. Biol. Chem.* 268:2836–2843 (1993) for details of these clones or their mouse homologs). The clones were transformed into appropriate host bacteria and plasmid preparations were made with conventional DNA purification techniques. A sample of each clone was linearized by restriction enzyme digestion and cRNA was synthesized with T3 RNA polymerase. The cRNA was diluted to 400 ng/µl and stored in 1 µl aliquots at −80° C. until injection.

The Xenopus oocyte expression system. Mature female *Xenopus laevis* were anaesthetized (20–40 min) using 0.15% 3-aminobenzoic acid ethyl ester (MS-222) and 2–4 ovarian lobes were surgically removed. Oocytes at developmental stages IV–VI (Dumont, J. N., *J. Morphol.* 136:153–180 (1972)), were dissected from the ovary still surrounded by enveloping ovarian tissues. Follicle-enclosed oocytes were micro-injected with 1:1 mixtures of cRNA:NR1A+NR2A, 2B, 2C or 2D; injecting ~2,5, or 20 ng of RNA encoding each receptor subunit. NR1A encoding cRNA was injected alone at ~20 ng. Oocytes were stored in Barth's medium containing (in mM):NaCl, 88; KCl, 1; $CaCl_2$, 0.41; $Ca(NO_3)_2$, 0.33; $MgSO_4$, 0.82 $NaHCO_3$, 2.4; HEPES 5, pH 7.4, with 0.1 mg/ml gentamicin sulphate. While oocytes were still surrounded by enveloping ovarian tissues the Barth's medium was supplemented with 0.1% bovine serum. Oocytes were defolliculated 1–2 days following injections by treatment with collagenase (0.5 mg/ml Sigma Type I for 0.5–1 hr) (Miledi and Woodward, *J. Physiol.* (Lond.) 416:601–621 (1989)) and subsequently stored in serum-free medium.

Electrical recordings were made using a conventional two-electrode voltage clamp (Dagan TEV-200) over periods ranging between 3–14 days following injection.

(Woodward et al., *Mol. Pharmacol.* 41:89–103 (1992)). Oocytes were placed in a 0.1 ml recording chamber continuously perfused (5–15 ml $min^{-1}$) with frog Ringer's solution containing (in mM):NaCl, 115; KCl, 2; $CaCl_2$, 1.8; HEPES, 5; pH 7.4. Drugs were applied by bath perfusion. Using oocytes expressing different subunit combinations of NMDA receptor, NMDA currents were activated by co-application of glutamate and glycine. Inhibitory potency of the novel antagonists was assessed on responses elicited by fixed concentrations of glutamate and glycine, by measuring reductions in current induced by progressively increasing concentrations of antagonists.

Concentration-inhibition curves were fit with equation 1.

$$I/I_{control}=1/(1+([antagonist]/10^{-pIC50})^n) \quad \text{Eq. 1}$$

in which $I_{control}$ is the current evoked by agonists alone, $pIC_{50}=-\log IC_{50}$, $IC_{50}$ is the concentration of antagonist that produces half maximal inhibition, and n is the slope factor. (De Lean et al., *Am. J. Physiol.* 235:E97-E102(1978)). For incomplete curves analysis by fitting was unreliable and $IC_{50}$ values were calculated by simple regression over linear portions of the curves (Origin: Microcal Software).

Maximal Electroshock-induced Seizures

Seizures were induced by application of current (50 mA, 60 pulses/sec, 0.8 sec pulse width, 1 sec duration, d.c.) through saline-coated corneal electrodes using a Ugo Basile ECT device (Model 7801). Mice were restrained by gripping the loose skin on their dorsal surface, electrodes were held lightly against the two cornea, then current was applied and mice were observed for a period of up to 30 sec for the occurrence of a tonic hindlimb extensor response. A tonic seizure was defined as a hindlimb extension in excess of 90 degrees from the plane of the body. Results were treated in a quantal manner.

The examples which follow are intended as an illustration of certain preferred embodiments of the invention, and no limitation of the invention is implied.

EXAMPLE 1

2-Benzylpiperdine Hydrochloride

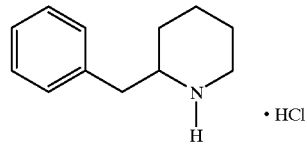

A solution of 2-benzylpyridine (2.0 g, 12 mmol) in MeOH (50 mL) containing conc. HCl (1 mL) was hydrogenated in a Parr apparatus over Pt ($PtO_2$, 30 mg) at 25° C. The reaction was allowed to proceed at 22 psi for 5 h, 45 psi for 4 h, then overnight at 22 to 12 psi. The catalyst was removed by filtration and the solvent was removed in vacuo to give a syrup. Absolute EtOH (50 mL) was added and then evaporated in vacuo. This was repeated to give a near colorless solid. The solid was triturated with ether (2×20 mL) and dried in vacuo to give a colorless powder (2.36 g, 94% yield); mp 128–131° C., lit. 125–130° C. (vide supra); $^1H$ NMR ($D_2O$) 1.45–2.05 (m, 6H), 2.80–3.05 (m, 3H), 3.27–3.45 (m, 2H) 7.26–7.46 (m, 5H).

EXAMPLE 2

1,2-Dibenzylpiperidine, Hydrobromide

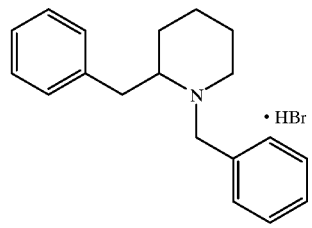

A mixture of 2-benzylpiperidine hydrochloride (500 mg, 2.36 mmol), $K_2CO_3$ (652 mg, 4.72 mmol) and benzyl bromide (605 mg, 3.54 mmol) in $CH_3CN$ (25 mL) was stirred at reflux under $N_2$ for 48 h. The reaction was allowed to cool to room temperature and was added to 5% aqueous HCl (100 mL). The resulting cloudy solution was extracted with $CHCl_3$ (3×50 mL). The extract was washed with 10% aqueous $NH_4OH$ (2×50 mL) and water (2×50 mL), filtered through cotton and the solvent removed in vacuo. Purification was effected by silica gel chromatography (2.5×30 cm) column, $CHCl_3$ elution). Solvent removal from the pure fractions yielded a cloudy amber oil. This was dissolved in MeOH (5 mL, cloudy solution), filtered through celite (clear solution) and the MeOH removed in vacuo to yield a clear amber oil (304 mg, 48%); $^1$H NMR (CDCl$_3$) 1.20–1.70 (m, 6H), 2.15–2.30 (m, 1 H), 2.58–2.82 (m, 3 H), 3.11–3.25 (m, 1 H), 3.49 (d, J=13.5 Hz, 1 H), 4.06 (d, J=13.5 Hz, 1 H), 7.10–7.41 (m, 10 H).

A solution of the free base (250 mg, 942 mmol) in MeOH (5 mL) was treated with a dilute solution of HBr in MeOH until the amine solution became permanently acidic (pH paper). The solvent was removed in vacuo to give an oil. This was dissolved in benzene (20 mL) and evaporated in vacuo. The resulting oil was dissolved in benzene and the solution added drop wise to vigorously stirred hexanes (175 mL). The resulting precipitate was collected, washed with hexanes (3×2 mL) and dried in vacuo to yield a beige powder (227 mg, 70%, mp 170–172° C.; $^1$H NMR (CDCl$_3$) 1.15–4.70 (m, 13 H), 7.08–7.90 (m, 10 H), 11.55 (bs, 1 H).

EXAMPLE 3

2-Benzyl-1-(2-phenylethyl)piperidine, Hydrobromide

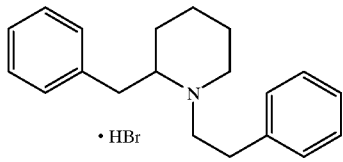

• HBr

From a mixture of 2-benzylpiperidine hydrochloride (500 mg, 2.36 mmol), K$_2$CO$_3$ (652 mg, 4.72 mmol) and 2-bromoethylbenzene (655 mg, 3.54 mmol) in CH$_3$CN (25 mL) there was obtained the free base as a clear amber oil (414 mg, 63%,); $^1$H NMR (CDCl$_3$) 1.18–1.89 (m, 6 H), 2.46–3.08 (m, 8 H), 3.15 (dd, J1=12.9 Hz, J2=3.6 Hz, 1 H), 7.14–7.36 (m, 10 H).

The HBr salt was a colorless powder; mp 155–158° C.; $^1$H NMR (CDCl$_3$) 1.30–3.78 (m, 15 H), 7.14–7.38 (m, 10 H), 11.50 & 11.69 (overlapping bs, 1 H).

An analytical sample was prepared by crystallization from 2-butanone; mp 162.5–164.5° C. Anal. Calcd. for C$_{20}$H$_{26}$BrN; C, 66.66; H, 7.27; N, 3.89. Found: C, 66.91; H, 7.18; N, 3.84.

EXAMPLE 4

2-Benzyl-1-(3-phenylpropyl)piperidine, Hydrobromide

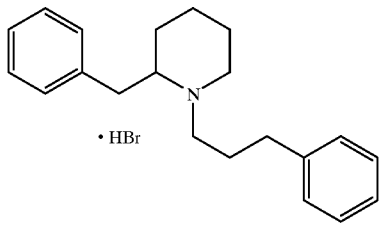

• HBr

From a mixture of 2-benzylpiperidine hydrochloride (500 mg, 2.36 mmol), K$_2$CO$_3$ (652 mg, 4.72 mmol) and 3-phenylpropyl bromide (705 mg, 3.54 mmol) in CH$_3$CN (25 mL) there was obtained the free base as a clear amber oil (425 mg, 61%); $^1$H NMR (CDCl$_3$) 1.10–1.70 (m, 6 H), 1.86 (m, 2H), 2.30–2.90 (m, 8 H), 3.30 (dd, J1=12.6 Hz, J2=3.0 Hz, 1 H), 7.10–7.35 (m, 10 H).

The HBr salt was colorless powder; mp 153–155° C.; $^1$H NMR (CDCl$_3$) γ 1.20–3.70 (m, 17 H), 7.08–7.36 (m, 10 H), 11.30 (bs, 1 H).

Analytical sample mp 155–157° C. Anal. Calcd. for C$_{20}$H$_{28}$BrN: C, 67.38; H, 7.54; N, 3.74. Found: C, 67.19; H, 7.73; N, 3.75.

EXAMPLE 5a

2-Benzyl-1-(4-phenylbutyl)piperidine), Citric Acid Salt

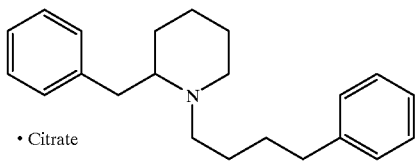

• Citrate

From 2-benzylpiperidine hydrochloride (250 mg, 1.18 mmol), K$_2$CO$_3$ (326 mg, 2.36 mmol) and 1-phenyl-4-tosylbutane (449 mg, 1.50 mmol) in CH$_3$CN (25 mL) there was obtained the free base as a clear amber oil; (286 mg, 79%) $^1$H NMR (CDCl$_3$) 1.15–1.75 (m, 10 H), 2.30–2.90 (m, 8 H), 3.09 (dd, J1=12.6 Hz, J2=2.7 Hz, 1 H), 7.11–7.37 (m, 10 H); HRMS calcd for C$_{22}$H$_{29}$N: 307.2299. Found: 307.2317.

A solution of the free base (272 mg, 885 mmol) in MeOH (5 mL) was combined with a solution of citric acid monohydrate (195 mg, 929 mmol) in MeOH (5 mL). The resulting solution was stirred for 5 min and the solvent was removed in vacuo to give a foamy solid. This was triturated with ether (10 mL) to give a powdery solid. The solid was collected, washed with ether (10×1 mL, tacky at this point) and dried in vacuo (0.05 Torr, 40° C.). The material became a solid mass during drying. Scraping with a spatula gave a powder (295 mg, 67%); mp 43–57° C.; $^1$H NMR (D$_2$O) 1.40–2.00 (m, 10H), 2.60–3.75(m, 13 H), 7.15–7.50 (m, 10 H).

EXAMPLE 5b

2-Benzyl-1-(4-phenylbutyl)piperidine, Hydrobromide

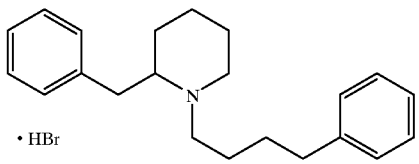

• HBr

The HBr salt was obtained as a colorless powder; mp 133–135° C.; $^1$H NMR (CDCl$_3$) 1.40–3.65 (m, 19 H), 7.04–7.35 (m, 10 H), 11.25 (bs, 1 H).

EXAMPLE 6a

2-Benzyl-1-(2-phenoxyethyl)piperidine, Citric Acid Salt

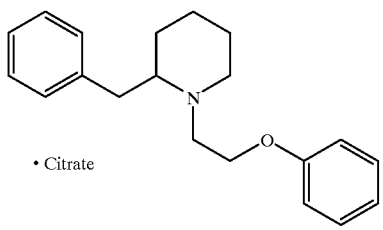

From 2-benzylpiperidine hydrochloride (500 mg, 2.36 mmol), 2-phenoxyethyl tosylate (1.04 g, 3.54 mmol and $K_2CO_3$ (652 mg, 4.72 mmol) there was obtained the free base as a clear amber oil; (417 mg, 60% $^1$H NMR (CDCl$_3$) 1.10–1.70 (m, 6 H), 2.4–3.3 (m, 7H), 4.12 (m, 2 H), 6.90–7.32 (m, 10 H); HRMS calcd for $C_{20}H_{25}NO$; 295.1936. Found: 295.1950.

The citric acid salt was obtained as a powder; mp 55–75° C.; $^1$H NMR (D$_2$O) 1.35–2.00 (m, 6 H), 2.70–4.05 (m, 11 H), 4.3–4.5 (m, 2 H), 6.90–7.45 (m, 10 H); IR (KBr) 2952, 1729, 1599, 1588, 1497, 1400, 1239, 1082, 756, 701, 692 cm$^{-1}$.

EXAMPLE 6b

2-Benzyl-1-(2-phenoxyethyl)piperidine Hydrobromide

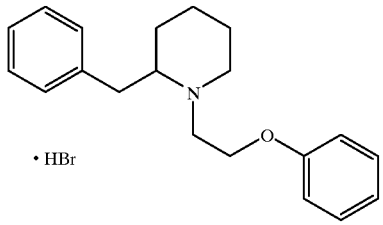

The HBr salt was obtain as a colorless powder; mp 119–121° C.; $^1$H NMR (CDCl$_3$) 1.30–4.80 (m, 15 H), 6.85–7.35 (m, 10 H), 11.57 and 11.74 (overlapping broad singlets, 1 H).

Analytical sample; mp 117–120° C. Anal. Calcd. for $C_{21}H_{28}BrNO$: C, 64.61; H, 7.23; N, 3.59. Found: C, 64.58; H, 7.24; N, 3.62.

EXAMPLE 7

2-Benzyl-1-(3-phenoxypropyl)piperidine Hydrobromide

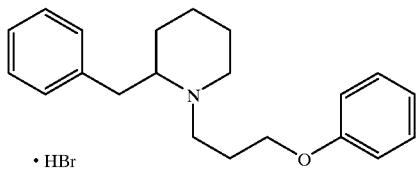

From a mixture of 2-benzylpiperidine hydrochloride (500 mg, 2.36 mmol), $K_2CO_3$ (652 mg, 4.72 mmol) and 3-phenoxypropyl bromide (761 mg, 3.54 mmol) in CH$_3$CN (25 mL) there was obtained the free base as a clear amber oil; (598 mg, 82%); $^1$H NMR (CDCl$_3$) 1.10–1.70 (m, 6 H), 1.95–2.08 (m, 2 H), 2.32–3.04 (m, 6 H), 3.10 (dd, J1=12.6 Hz,J2=3.0 Hz, 1 H), 4.01 (t, J=6.3 Hz, 2 H), 6.88–7.32 (m, 10 H).

The HBr salt was obtained as a colorless powder; mp 119–121° C.; $^1$H NMR (CDCl$_3$) 1.45–2.21 (m, 6 H), 2.40–2.79 (m, 3 H), 3.15–3.72 (m, 6 H), 4.15 (t, J=5.25 Hz, 2 H), 6.85–7.35 (m, 10 H), 11.47 (bs, 1 H). Anal. Calcd. for $C_{21}H_{28}BrNO$: C, 64.61; H, 7.23; N, 3.59. Found: C, 64.58; H, 7.24; N, 3.62.

EXAMPLE 8a

2-Benzyl-1-(4-phenoxybutyl)piperidine, Citric Acid Salt

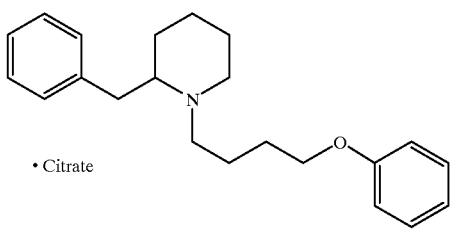

From 2-benzylpiperidine hydrochloride (500 mg, 2.36 mmol) and $K_2CO_3$ (652 mg, 4.72 mmol) and 4-phenoxybutyl bromide (811 mg, 3.54 mmol) in CH$_3$CN (50 mL), there was obtained the free base as a clear amber oil; (594 mg, 78); $^1$H NMR (CDCl$_3$) 1.10–1.90 (m, 10 H), 2.30–2.90 (m, 6 H), 3.10 (dd, J1=12.9 Hz, J2=3.0 Hz, 1 H), 4.01 (t, J=6.0 Hz, 2 H), 6.88–7.34 (m, 10 H); HRMS calcd for $C_{22}H_{29}NO$: 323.2249. Found: 323.2259.

The citric acid salt was obtained as a beige powder; mp 42–56° C.; $^1$H NMR (D$_2$O) 1.45–2.10 (m, 10 H), 2.80–3.80 (m, 11 H), 4.05–4.25 (m, 2 H), 6.95–7.50 (m, 10 H).

EXAMPLE 8b

2-Benzyl-1-(4-phenoxybutyl)piperidine Hydrobromide

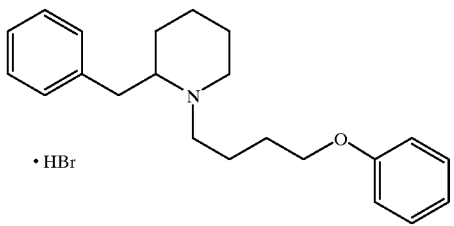

HBr salt was obtained as a a colorless powder; mp 100–103° C.; $^1$H NMR (CDCl$_3$) 1.25–3.70 (m, 17 H), 3.92–4.10 (m, 2 H), 6.81–7.35 (m, 10 H), 11.27 (bs, 1 H). Anal. Calcd. for $C_{22}H_{30}BrNO$: C, 65.34; H, 7.48; N, 3.46. Found: C, 65.29; H, 7.78; N, 3.41.

EXAMPLE 9

4-(o-(Trifluoromethyl)phenoxy)-1-bromobutane

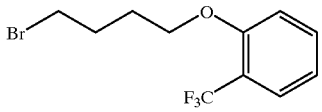

A mixture of α,α,α-trifluoro-p-cresol (2.22 g, 13.7 mmol), K$_2$CO$_3$ (1.99 g, 14.4 mmol) and 1,4-dibromobutane (14.5 g, 68.5 mmol) in CH$_3$CN (50 mL) was stirred at reflux under N$_2$ for 24 h. The reaction was allowed to cool to 25° C. and then added to water (100 mL). The resulting biphasic mixture was extracted with CHCl$_3$ 3×50 mL). The extract was washed with water (1×50 mL), saturated NaHCO$_3$ (2×50 mL) and water (1×50 mL), filtered through cotton and the solvent removed in vacuo to give an orange liquid. The excess 1,4-dibromobutane was removed by vacuum distillation (5 Torr, 72–78° C.). The still pot residue, which contained the product was subjected to chromatography on silica gel (2.5×30 cm) with CHCl$_3$ elution, yielded a colorless liquid; (2.75 g, 68%); $^1$H NMR (CDCl$_3$) 1.89–2.17 (m, 4 H), 3.50 (t, J=6.3 Hz, 2 H), 4.09 (t, J=5.7 Hz, 2 H), 6.92–7.05 (m, 2 H), 7.48 (t, J=7.8 Hz, 1 H), 7.56 (d, J=7.8 Hz, 1 H).

EXAMPLE 10

2-Benzyl-1-(4-(o-(trifluoromethyl) phenoxy)butyl) piperidine Hydrobromide

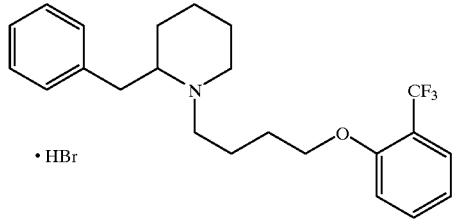

From 2-benzylpiperidine hydrochloride (500 mg, 2.36 mmol), K$_2$CO$_3$ (652 mg, 4.72 mmol) and 4-(o-(trifluoromethyl)phenoxy)-1-bromobutane (841 mg, 2.83 mmol) in CH$_3$CN (25 mL) there was obtained the free bases as a clear amber oil; (570 mg, 62%), $^1$H NMR (CDCl$_3$) 1.15–1.90 (m, 10 H), 2.35–2.95 (m, 6 H), 3.09 (dd, J1=12.6 Hz, J2=2.7 Hz, 1 H), 4.08 (t, J=5.4 Hz, 2 H), 6.93–7.31 (m, 7 H), 7.47 (t, J=5.1 Hz, 1 H), 7.56 (d, J=7.5 Hz, 1 H).

The HBr salt was obtained as a colorless powder; mp 136–140° C.; $^1$H NMR (CDCl$_3$) 1.25–3.69 (m, 17 H), 4.02–4.21 (m, 2 H), 6.94–7.34 (m, 7 H), 7.50 (t, J=7.8 Hz, 1 H), 7.56 (d, J=7.8 Hz, 1 H), 11.24 (bs, 1 H). Anal. Calcd. for C$_{23}$H$_{29}$BrF$_3$NO: C, 58.48; H, 6.19; N, 2.97. Found: C, 58.81; H, 6.32; N, 2.87.

EXAMPLE 11

4-(m-(Trifluoromethyl)phenoxy)-1-bromobutane

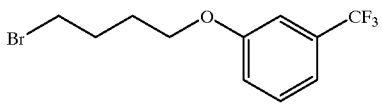

From a mixture of α,α,α-trifluoro-p-cresol (5.00 g, 30.8 mmol), K$_2$CO$_3$ (4.47 g, 32.3 mmol) and 1,4-dibromobutane (33.3 g, 154 mmol) in CH$_3$CN (250 mL) there was obtained the bromide as a near colorless liquid; (7.50 g, 82% $^1$H NMR (CDCl$_3$) 1.89–2.15 (m, 4 H), 3.50 (t, J=6.3 Hz, 2 H), 4.03 (t, J=6.0 Hz, 2 H), 7.03–7.25 (m, 3 H), 7.38 (dd, J1=7.9, J2=8.0 Hz, 1 H).

EXAMPLE 12

2-Benzyl-1-(4-(m-(trifluoromethyl)phenoxy)butyl) piperidine, Hydrobromide

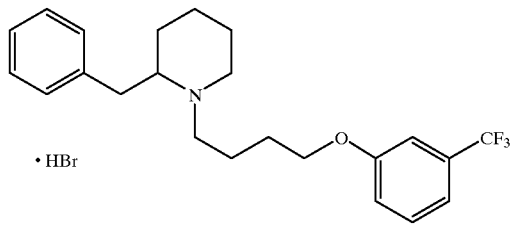

From a mixture of 2-benzylpiperidine hydrochloride (500 mg, 2.36 mmol), K$_2$CO$_3$ (652 mg, 4.72 mmol) and 4-(m-(trifluoromethyl)phenoxy)-1-bromobutane (1.05 g, 3.54 mmol) in CH$_3$CN (25 mL) there was obtained the free base as a clear amber oil; (672 mg, 72%); $^1$H NMR (CDCl$_3$) 1.15–1.91 (m, 10 H), 2.29–2.89 (m, 6 H), 3.07 (dd, J1=9.8 Hz, J2=3.2 Hz, 1 H), 4.01 (t, J=6.0 Hz, 2 H), 7.01–7.41 (m, 9 H).

The HBR salt was obtained as a colorless powder; mp 142.5–144° C.; $^1$H NMR (CDCl$_3$) 1.25–3.70 (m, 17 H), 3.95–4.12 (m, 2 H), 7.00–7.18 (m, 9 H), 11.40 (bs, 1 H); Analytical sample; mp 143.5–144.5° C. Anal. Calcd. for C$_{23}$H$_{29}$BrF$_3$NO: C, 58.48; H, 6.19; N, 2.97. Found: C, 58.38; H, 6.23; N, 2.87.

EXAMPLE 13

4-(p-(Trifluoromethyl)phenoxy)-1-bromobutane

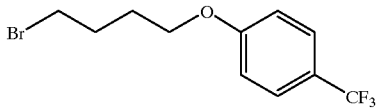

From a mixture of α,α,α-trifluoro-p-cresol (5.04 g, 31.1 mmol), K$_2$CO$_3$ (4.50 g, 32.6 mmol) and 1,4-dibromobutane (18.5 mL, 33.5 g, 155 mmol) in CH$_3$CN (100 mL) there was obtained a colorless liquid; (6.70 g, 72%, $^1$H NMR (CDCl$_3$) 1.89–2.15 (m, 4 H), 3.50 (t, J=6.3 Hz, 2 H), 4.03 (t, J=6.0 Hz, 2 H), 6.94 (d, J=8.4 Hz, 2 H), 7.54 (d, J=8.4 Hz, 2 H).

EXAMPLE 14

2-Benzyl-1-(4-(p-(trifluoromethyl)phenoxy)butyl)piperidine, Hydrobromide

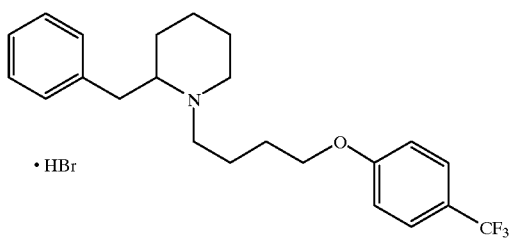

From a mixture of 2-benzylpiperidine hydrochloride (500 mg, 2.36 mmol, K$_2$CO$_3$ (652 mg, 4.72 mmol) and 4-(p-(trifluoromethyl)phenoxy)-1-bromobutane (1.05 g, 3.54 mmol) in CH$_3$CN (25 mL) there was obtained the free base as a clear amber oil; (610 mg, 66%), $^1$H NMR (CDCl$_3$) 1.15–1.91 (m, 10 H), 2.29–2.89 (m, 6 H), 3.07 (dd, J1=12.9 Hz, J2=3.2 Hz, 1 H), 4.02 (t, J=6.00 Hz, 2 H); 6.95 (d, J=8.7 Hz, 2 H), 7.12–7.32 (m, 5 H), 7.54 (d, J=8.4 Hz, 2 H).

The HBr salt was obtained as a colorless powder; mp 130–134° C.; $^1$H NMR (CDCl$_3$) 1.25–3.70 (m, 17 H), 3.95–4.12 (m, 2 H), 6.88–6.95 (m, 2 H), 7.14–7.37 (m, 5 H), 7.54 (d, J=8.4 Hz, 2 H), 11.33 (bs, 1 H). Anal. Calcd. for C$_{23}$H$_{29}$BrF$_3$NO: C, 58.48; H, 6.19; N, 2.97. Found: C, 58.52; H, 6.25; N, 2.85.

EXAMPLE 15

4-(m-Fluorophenoxy)-1-bromobutane

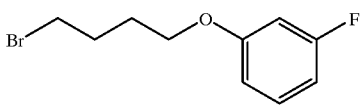

From a mixture of 3-fluorophenol (5.00 g, 44.6 mmol), K$_2$CO$_3$ (6.47 g, 48.6 mmol) and 1,4-dibromobutane (26.6 mL, 48.1 g, 223 mmol) in CH$_3$CN (200 mL) there was obtained the bromide as a colorless liquid; (7.30 g, 66%); $^1$H NMR (CDCl$_3$) 1.89–2.15 (m, 4 H), 3.49 (t, J=6.3 Hz, 2 H), 3.99 (t, J=6.0 Hz, 2 H), 6.55–6.71 (m, 3 H), 7.21 (dd, J1=J2=7.8 Hz, 1 H).

EXAMPLE 16

2-Benzyl-1-(4-(m-fluorophenoxy)butyl)piperidine, Hydrobromide

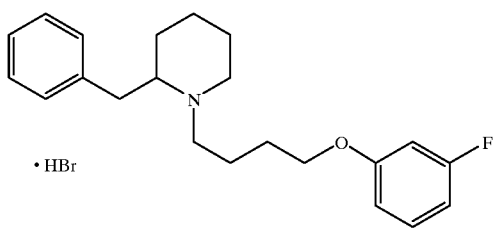

From a mixture of 2-benzylpiperidine hydrochloride (500 mg, 2.36 mmol), K$_2$CO$_3$ (652 mg, 4.72 mmol) and 4-(m-fluorophenoxy)-1-bromobutane (874 mg, 3.54 mmol) in CH$_3$CN (25 mL) there was obtained the free base as a clear amber oil; (610 mg, 76%) $^1$H NMR (CDCl$_3$) 1.10–1.95 (m, 10 H), 2.28–2.95 (m, 6 H), 3.12 (dd, J1=12 Hz, J2=3.3 Hz, 1 H), 4.00 (t, J=6.0 Hz, 2 H); 6.60–6.75 (m, 4 H), 7.15–7.36 (m, 5H).

The HBr salt was obtained as a colorless powder; mp 119–123° C.; $^1$H NMR (CDCl$_3$) 1.20–3.75 (m, 17 H), 3.95–4.12 (m, 2 H), 6.55–6.72 (m, 3 H), 7.14–7.37 (m, 6 H), 11.31 (bs, 1 H). Anal. Calcd. for C$_{22}$H$_{29}$BrFNO: C, 62.56; H, 6.92; N, 3.32. Found: C, 62.58; H, 6.89; N, 3.28.

EXAMPLE 17

2-[(2-Ethoxy)phenyoxy]methyl-1-(3-phenoxy)propylpiperidine

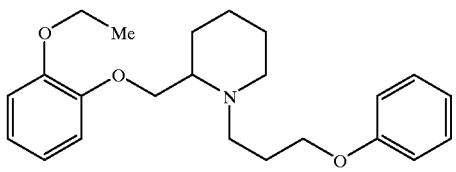

A mixture of 2-[(2-ethoxy)phenoxymethylpiperidine (3 mmol), 1-bromo-3-phenoxypropane (5 mmol) and potassium carbonate (1 g) in acetonitrile (200 mL) was heated at reflux for 6 h. After diluting with water, the product was extracted with chloroform and purified by column chromatography.

EXAMPLE 18

2-Benzyl-1-[2-hydroxy-3-(2-methyl)phenoxy]propylpiperidine

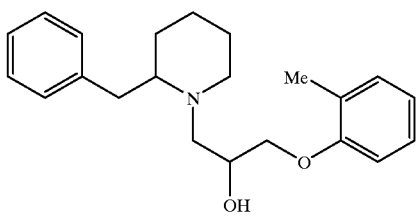

A mixture of 2-benzylpiperidine (2 mmol) and 3-(2-methylphenoxy)propaneoxide (3 mmol) in acetonitrile was heated at 60° C. for 12 h. The solvent was removed by rotoevaporation, and the product purified by column chromatography.

EXAMPLE 19

2-[1-hydroxy-2-phenyl]ethyl-1-(3-phenoxy)-propylpiperidine

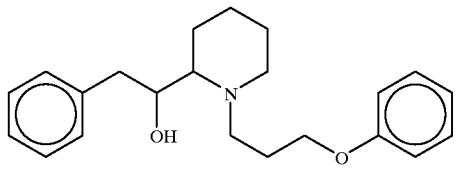

A mixture of 1-benzyl-2-piperidine carboxaldehyde and benzyl magnesium bromide in tetrahydrofuran is reacted at about 0° C. under a nitrogen atmosphere. The reaction is quenched with water and the reaction product 2-[1-hydroxy-2-phenyl]ethyl-1-phenylpiperidine is treated with 10% palladium on carbon under a hydrogen atmosphere to provide 2-[1-hydroxy-2-phenyl]ethylpiperidine. A mixture of this reaction product, 1-bromo-3-phenoxypropane and potassium carbonate in acetonitrile is heated at reflux for about 6 hours to provide the titled compound.

EXAMPLE 20

2-Benzyl-1-(5-phenoxypentyl)piperidine Hydrobromide

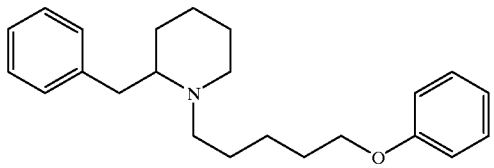

A) 1-Bromo-5-phenoxypentane. From a mixture of phenol (1.00 g, 10.6 mmol,) $K_2CO_3$ (1.52 g, 11.0 mmol, and 1,5-dibromopentane (12.2 g, 53 mmol, ) in $CH_3CN$ (50 mL) there was obtained a colorless liquid; (1.47 g, 57%); $^1H$ NMR ($CDCl_3$) 1.55–2.02 (m, 6 H), 3.45 (t, J=6.6 Hz, 2 H), 3.98 (t, J=6.3 Hz, 2 H), 6.87–6.97 (m, 3 H), 7.24–7.33 (m, 2 H).

B) 2-Benzyl-1-(5-phenoxypentyl)piperidine hydrobromide. From a mixture of 2-benzylpiperidine hydrochloride (500 mg, 2.36 mmol), $K_2CO_3$ (652 mg, 4.72 mmol, ) and 1-bromo-5-phenoxypentane (860 mg, 3.54 mmol) in $CH_3CN$ (25 mL) there was obtained the free amine as a clear amber oil; (568 mg, 71%); $^1H$ NMR ($CDCl_3$), 1.15–1.90 (m, 12 H), 2.29–2.89 (m, 6 H), 3.08 (dd, J1=12.6 Hz, J2=3.3 Hz, 1 H), 3.97 (t, J=6.3 Hz, 2 H), 6.85–7.33 (m, 10 H).

The hydrobromide salt was obtained as a colorless powder mp 137.5–139.5° C. $^1H$ NMR ($CDCl_3$) 1.25–3.68 (m, 19 H), 3.88–4.05 (m, 2 H), 6.84–7.35 (m, 10 H), 11.29 (bs, 1 H). Anal. Calcd for $C_{23}H_{32}BrNO$: C, 66.02; H, 7.71; N. 3.35. Found: C, 66.23; H. 7.72; N. 3.31.

EXAMPLE 21

2-Benzyl-1-(2-(4-nitrophenoxy)ethyl)piperidine Hydrobromide

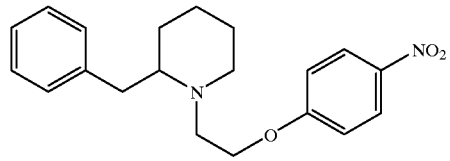

A) 1-Bromo-2-(4-nitrophenoxy)ethane. From a mixture of 4-nitrophenol (10.0 g, 71.9 mmol), $K_2CO_3$ (10.4 g, 75.5 mmol) and 1,2-dibromoethane (31.0 mL, 67.6 g, 360 mmol in dimethylformamide (DMF) (50 mL) there was obtained a very pale yellow solid; (6.77 g, 38%); mp 64–66° C.; $^1H$ NMR ($CDCl_3$) 3.68 (t, J=6.0 Hz, 2 H), 4.39 (t, J–6.0 HZ, 2 H), 6.99 (d, J=9.3 Hz, 2 H), 8.22 (d, J=9.3 Hz, 2 H).

B) 2-Benzyl-1-(2-(4-nitrophenoxy)ethyl)piperidine hydrobromide. From a mixture of 2-benzylpiperidine hydrochloride (1.00 g, 4.72 mmol), $K_2CO_3$ (1.30 g, 9.44 mmol) and 1-bromo-2-(4-nitrophenoxy)ethane (1.17 g, 4.96 mmol) in $CH_3CN$ (50 mL) there was obtained the hydrobromide as a pale yellow solid (888 mg, 45%); mp 180–182° C., $^1H$ NMR ($CDCl_3$) 1.35–2.42 (m, 6 H), 2.75–405 (m, 7 H), 4.50–4.95 (m, 2 H), 6.95–7.37 (m, 7H), 8.15–8.26 (m, 2 H), 11.72 and 11.88 (overlapping bs, 1 H). Anal. Calcd for $C_{20}H_{25}BrN_2O_3$: C, 57.01; H, 5.98: N, 6.65. Found: C, 57.16; H, 6.01; N, 6.61.

EXAMPLE 22

1-(2-(4-Aminophenoxy)ethyl)-2-benzylpiperidine Dihydrobromide

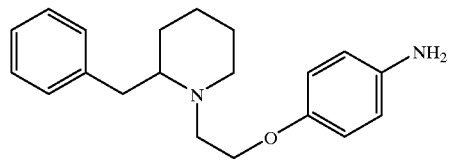

A mixture of 2-benzyl-1-(2-(4-nitrophenoxy)ethyl) piperidine hydrobromide (500 mg, 1.19 mmol) and Pd/C (10%, 50 mg, Aldrich) in MeOH (25 mL) was shaken under $H_2$ (20–30 psi, Parr) for 2 h at 25° C. The catalyst was removed by filtration (Celite). The resulting solution was acidified with a dilute solution of HBr in MeOH (pH paper to red). The MeOH was removed in vacuo (rotoevaporator, 35–40° C.) to give a syrup. Ether (45 mL) was added and the resulting mixture was vigorously stirred at 25° C. for 24 h. A yellow suspension was obtained. The solid was collected, washed with ether (3×2 mL) and dried in vacuo (0.005 Torr, 56° C.) to give a beige powder (358 mg, 64%): mp 130° C.; $^1H$ NMR (DMSO-$d_6$) 1.28–1.95 (m, 6 H), 2.69–3.95 (m, 7 H), 4.60–4.55 (m, 2 H), 7.08–7.42 (m, 9 H), 9.60–10.25 (m, 4 H); HRMS Calcd for $C_{20}H_{26}N_2O$: 310.2045. Found: 310.2040.

EXAMPLE 23

2-(4-Chlorobenzyl)-1-(2-(4-fluorophenoxy)ethyl)
pyridinium Bromide

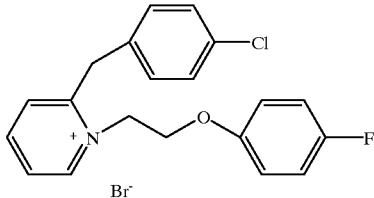

From a solution of 2-(4-chlorobenzyl)pyridine (500 mg, 2.45 mmol) and 2-(4-fluorophenoxy)ethyl bromide (537 mg, 2.45 mmol) in $CH_3CN$ (5 mL) was obtained the title compound as a colorless powder (271 mg, 26%), mp 179–180° C.; $^1$H NMR ($CDCl_3$) 4.56 (t, J=4.8 Hz, 2H), 4.91 (s, 2H), 5.57 (t, J=4.8 Hz, 2H), 6.74–6.81 (m, 2H), 6.89–6.97 (m, 2H), 7.23–7.30 (m, 2H), 7.36–7.40 (m, 2H), 7.50 (dd, J=8.1 and 1.2 Hz, 1H), 7.96 (dt, J=6.9 and 1.2 Hz, 1H), 8.28 (dt, J=7.8 and 1.5 Hz, 1H), 9.31 (dd, J=6.0 and 1.2 Hz, 1H); Anal. Calcd for $C_{20}H_{18}BrClFNO \cdot H_2O$: C, 54.50; H, 4.57; N, 3.18. Found: C, 54.70; H, 4.38; N, 3.14.

EXAMPLE 24

2-(4-Chlorobenzyl)-1-(2-(4-fluorophenoxy)ethyl)
piperidine Hydrochloride

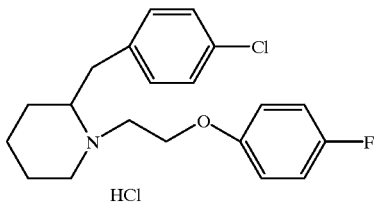

A) 2-(4-Chlorobenzyl)piperidine hydrochloride. A mixture of 2-(4-chlorobenzyl)pyridine (2.10 g, 10.3 mmol) in MeOH (50 mL) containing concd HCl (2 mL) and $PtO_2$ (30 mg) was hydrogenated (Parr) at 10 to 20 psi for 24 h at 25° C. The catalyst was removed by filtration (Celite). The solvent was removed from the filtrate to give an oil, which was further dried in vacuo ($H_2O$ aspirator, 60° C.) to give a solid. The solid was triturated with ether (50 mL) and was collected and dried in vacuo (100° C., 0.005 Torr) to yield the title compound as a pale beige powder (2.41 g, 95%): mp 172–175° C.; $^1$H NMR ($D_2O$) 1.38–1.72 (m, 3H), 1.77–2.02 (m, 3H), 2.83–3.03 (m, 3H), 3.36 (d, J=11 Hz, 2H), 7.26 (d, J=8.7 Hz, 2H), 7.40 (d, J=7.8 Hz, 2H).

B) 2-(4-Chlorobenzyl)-1-(2-(4-fluorophenoxy)ethyl) piperidine hydrochloride. From a mixture of 2-(4-chlorobenzyl)piperidine hydrochloride (500 mg, 2.03 mmol), 2-(4-fluorophenoxy)ethyl bromide (467 mg, 2.13 mmol) and $K_2CO_3$ (575 mg, 4.16 mmol) in $CH_3CN$ (20 mL) the free base of the title compound was obtained as an amber oil (445 mg, 63%): $^1$H NMR ($CDCl_3$) 1.15–1.35 (m, 2H), 1.42–1.70 (m, 4H), 2.42–3.20 (m, 7H), 3.95–4.13 (m, 2H), 6.82–7.02 (m, 4H), 7.10 (d, J=8.4 Hz, 2H), 7.24 (d, J=8.4 Hz, 2H).

The hydrochloride was obtained as a colorless powder (395 mg, 80%), mp 163–165° C.; $^1$H NMR ($CDCl_3$) 1.30–2.35 (m, 6H), 2.62–3.80 (m, 7H), 4.30–4.70 (m, 2H), 6.82–7.32 (m, 8H), 12.67 and 12.83 (overlapping bs, 1H); Anal. Calcd for $C_{20}H_{24}Cl_2FNO$: C, 62.51; H, 6.29; N, 3.64. Found: C, 62.51; H, 6.42; N, 3.47.

EXAMPLE 25

2-(4-Chlorobenzyl)-1-(2-(4-hydroxyphenoxy)ethyl)
piperidine Hydrochloride

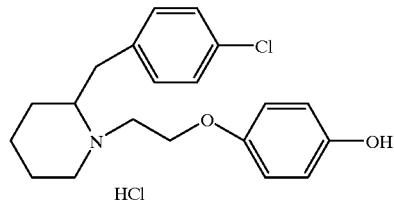

From a mixture of 2-(4-chlorobenzyl)piperidine hydrochloride (500 mg, 2.03 mmol), 2-(4-hydroxyphenoxy)ethyl bromide (462 mg, 2.13 mmol) and $NaHCO_3$ (349 mg, 4.16 mmol) in $CH_3CN$ (20 mL) was obtained the free base of the title compound as a foam (572 mg): $^1$H NMR ($CDCl_3$) 1.20–1.35 (m, 2H), 1.43–1.70 (m, 4H), 2.47–2.64 (m, 2H), 2.68–2.80 (m, 1H), 2.92–3.21 (m, 4H), 3.87–4.13 (m, 2H), 6.72 (d, J=9.3 Hz, 2H), 6.87 15. (bs, 1H), 6.76 (d, J=9.0 Hz, 2H), 7.08 (d, J=8.4 Hz, 2H), 7.24 (d, J=8.4 Hz, 2H).

The hydrochloride was obtained as a colorless powder (454 mg, 57%): mp 229–230° C.; $^1$H NMR (DMSO-$d_6$) 1.27–1.90 (m, 6H), 2.75–3.80 (m, 7H), 4.22–4.41 (m, 2H), 6.71 (d, J=7.2 Hz, 2H), 8.82 (d, J=9.0 Hz, 2H), 7.21–7.42 (m, 4H), 9.12 (s, 1H), 10.96 and 11.15 (overlapping bs, 1H); Anal. Calcd for $C_{20}H_{25}Cl_2NO_2$: C, 62.83; H, 6.59; N, 3.66. Found: C, 62.75; H, 6.59; N, 3.52.

EXAMPLE 26

2-Benzyl-1-(2-(4-hydroxyphenoxy)ethyl)piperidine
Hydrochloride

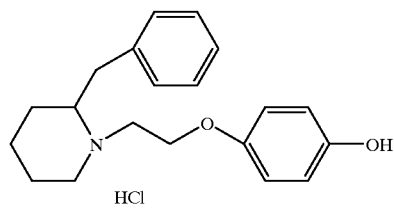

From a mixture of 2-benzylpiperidine hydrochloride (500 mg, 2.36 mmol), 2-(4-hydroxyphenoxy)ethyl bromide (614 mg, 2.83 mmol) and $NaHCO_3$ (407 mg, 4.84 mmol) in $CH_3CN$ (20 mL) was obtained the free base of the title compound as a brown oil (467 mg, 64%): $^1$H NMR ($CDCl_3$) 1.20–1.70 (m, 6 H), 2.50–2.61 (m, 2 H), 2.69–2.80 (m, 1 H), 2.93–3.06 (m, 2 H), 3.12–3.24 (m, 2 H), 3.99–4.13 (m, 2 H), 6.74 (s, 4 H), 7.14–7.31 (m, 5 H).

The hydrochloride was obtained as a colorless solid: mp 215–216° C.; $^1$H NMR ($CD_3OD$) 1.40–2.07 (m, 6 H), 2.70–4.43 (m, 9 H), 6.72–6.79 (m, 2 H), 6.85–6.92 (m, 2 H), 7.24–7.39 (m, 5 H); Anal. Calcd for $C_{20}H_{26}ClNO_2$: C, 69.04; H, 7.53; N, 4.03. Found: C, 69.02; H, 7.30, N, 3.95.

EXAMPLE 27

2-Benzyl-1-(3-(4-hydroxyphenoxy)propyl)piperidine Hydrochloride

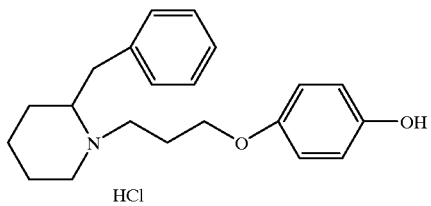

From a mixture of 2-benzylpyridine hydrochloride (500 mg, 2.36 mmol), 3-(4-hydroxyphenoxy)propyl bromide (654 mg, 2.83 mmol), and NaHCO$_3$ (407 mg, 4.84 mmol) in CH$_3$CN (20 mL) was obtained the free base of the title compound as a yellow oil (385 mg, 45%): $^1$H NMR (CDCl$_3$) 1.20–1.70 (m, 6 H), 1.93–2.04 (m, 2 H), 2.36–3.16 (m, 7 H), 3.90–3.98 (t, 2 H. J=6.15 Hz), 6.70–6.80 (m, 4 H), 7.12–7.30 (m, 5 H).

The hydrochloride was obtained as a light brown solid: mp 163–164° C.; $^1$H NMR (DMSO) 1.25–1.90 (m, 5 H), 2.10–2.30 (m, 2 H), 2.70–3.18 (m, 3 H), 3.20–3.62 (m, 5 H), 3.93–4.02 (m, 2 H), 6.64–6.84 (m, 4 H), 7.18–7.42 (m, 5 H), 8.99 (s, 1 H), 10.53–10.80 (d, 1 H, J=39.3); Anal. Calcd for C$_{21}$H$_{28}$ClNO$_2$: C, 69.69; H, 7.80; N, 3.87. Found: C, 69.70; H, 7.67; N, 3.83.

EXAMPLE 28

2-Benzyl-1-(4-(4-hydroxyphenoxy)butyl)piperidine Hydrochloride

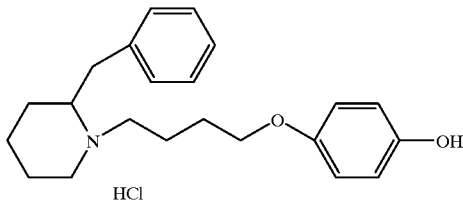

A) 4-(4-Benzyloxyphenoxy)butyl bromide. From a mixture of 4-(benzyloxy)phenol (11.7 g, 58.4 mmol), 1,4-dibromobutane (35.0 mL, 63.3 g, 293 mmol) and K$_2$CO$_3$ (8.07 g, 58.4 mmol) in CH$_3$CN (200 mL) was obtained the title compound as a tan solid (10.8 g, 55%): $^1$H NMR (CDCl$_3$) 1.86–1.98 (m, 2 H), 2.00–2.13 (m, 2 H), 3.44–3.53 (t, 2 H, J=6.6 Hz), 3.90–3.99 (t, 2 H, J=6.0 Hz), 5.02 (s, 2 H), 6.77–6.85 (m, 2 H), 6.85–6.94 (m, 2 H), 7.27–7.46 (m, 5 H).

B) 2-Benzyl-1-(4-(4-benzyloxyphenoxy)butyl)piperidine. From a mixture of 2-benzylpiperidine hydrochloride (1.00 g, 4.72 mmol), 4-(4-benzyloxyphenoxy)butyl bromide (1.90 g, 5.66 mmol), and NaHCO$_3$ (80.0 mg, 9.44 mmol) in CH$_3$CN (50 mL) was obtained the title compound as a yellow solid (428 mg, 21%), $^1$H NMR (CDCl$_3$) 1.22–2.42 (m, 9 H), 3.03–3.68 (m, 8 H), 3.89–4.02 (m, 2 H), 5.01 (s, 2 H), 6.74–6.94 (m, 4 H), 7.12–7.45 (m, 10 H).

C) 2-Benzyl-1-(4-(4-hydroxyphenoxy)butyl)piperidine hydrochloride. A mixture of 2-benzyl-1-(4-(4-benzyloxyphenoxy)butyl)piperidine (400 mg, 0.93 mmol) and Pd (40.0 mg, 10% on carbon) in MeOH (20 mL) was hydrogenated (40 psi) for 24 hours. The catalyst was removed by filtration and the solvent was removed from the filtrate to give a yellow oil. The oil was purified on silica gel (1.5×40 cm) with 10% EtOH in CHCl$_3$ elution to yeild the free base of the title compound as a pink oil (313 mg): $^1$H NMR (CDCl$_3$) 1.20–1.98 (m, 10 H), 2.62–3.29 (m, 7 H), 3.75–3.85 (t, 2 H, J=6.0 Hz), 6.63–6.72 (d, 2 H, J=8.7 Hz), 6.76–6.85 (d, 2 H, J=8.7 Hz), 7.12–7.33 (m, 5 H).

The hydrochloride was obtained as a colorless solid (185 mg, 53%): mp 161–162° C.; $^1$H NMR (DMSO-d$_6$) 1.28–1.94 (m, 10 H), 2.96–3.62 (m, 7 H), 3.90 (s, 2 H), 6.63–6.71 (d, 2 H, J=9.0 Hz), 6.71–6.79 (d, 2 H, J=8.7 Hz), 7.20–7.38 (m, 5 H), 8.95 (s, 1 H), 10.28–10.55 (m, 1 H).

EXAMPLE 29

1-[2-(4-amino-3-nitrophenoxy)ethyl]-2-benzylpiperidine

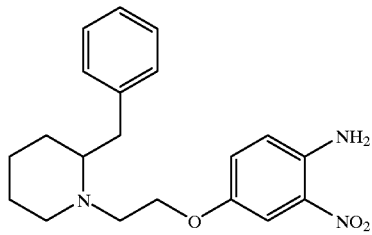

From a mixture of 2-benzyl-piperidine (1.08 mg, 6.16 mmol), (4-amino-3-nitrophenoxy)ethyl bromide (796 mg, 3.05 mmol) and NaI (100 mg) in toluene (25 mL) was obtained 738 mg (68%) of the title compound as a yellow powder, mp 174–6° C. $^1$H NMR (CDCl$_3$): 1.23–1.29 (m, 2H), 1.48–1.66 (m, 4H), 2.48–2.58 (m, 2H), 2.66–2.72 (m.1H), 2.93–3.02 (m, 2H), 3.11–3.20 (m, 2H), 4.06–4.10 (m, 2H), 6.759 (d, 1H, J=9), 7.092 (dd, 1H, J=9; 3), 7.16–7.30 (m, 5H), 7.959 (d, 1H, J=3).

EXAMPLE 30

2-Benzyl-1-(4-(2-oxobenzimidazol-5-oxy) ethyl) piperidine

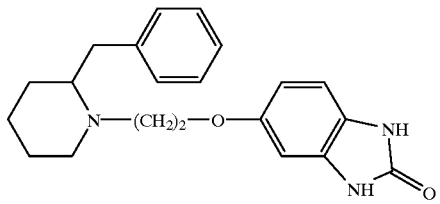

a) A mixture of of 1-[2-(4-amino-3-nitrophenoxy)ethyl]-2-benzylpiperidine (705 mg, 1.99 mmol) and Raney Ni (about 200 mg) in EtOH (15 mL) was shaken under H$_2$ (35–25 parr) for 4 h, then filtered. The filtrate was evapoated, and the residue was purified by chromatography over silica gel (CHCl$_3$—MeOH, 3:2) to give 2-benzyl-1-[(3,4-diaminophenoxy)ethyl]piperidine (650 mg, 98%) as a brown viscous oil. $^1$H NMR (CDCl$_3$): 1.22–1.32 (m, 2H), 1.49–1.52 (m, 3H), 2.49–2.56 (m, 2H), 2.756 (bs, 2H, NH$_2$), 2.96–3.06 (m, 2H), 3.13–3.24 (m, 2H), 3.520 (bs, 2H, NH2), 4.02–4.12 (m, 2H), 6.285 (dd, 1H, J=9; 3), 6.350 (d, 1H, J=3), 6.640 (d, 1H, J=9), 7.16–7.30 (m, 5H).

b) A mixture of 2-benzyl-1-[(3,4-diaminophenoxy)ethyl] piperidine (650 mg, 2.0 mmol) and CDI (390 mg, 2.4 mmol) in toluene (25 mL) was refluxed for 24 h, then cooled to r.t. The mixture was evaporated, and the residue was purified by chromatography over silica gel (CHCl₃—MeOH, 3:2) to give 422 mg (60%) of the title compound as a viscous oil. The hydrochloride is highly hygroscopic. $^1$H NMR (DMSO-$d_6$): 10.486 (s, 1H, NH), 10.650 (s, 1H, NH).

The data for the compounds of Examples 3, 4, 5, 6, 7, 8, 17, 18, 20, 21, 22, 24, 25, 26, 27, 28 and 30 described above in the expressed cloned NMDA subtypes is shown below in Table 1 along with maximal electroshock (MES) data for several compounds:

TABLE 1

| Compound | Subunits (IC$_{50}$ (μM)) | | | | MES (ED$_{50}$) (mg/kg) |
|---|---|---|---|---|---|
| | 1A/2A | 1A/2B | 1A/2C | 1A/2D | |
| Example 8 | 3 | 8 | 45 | | 4 |
| Example 7 | 4 | 12 | 45 | | 2.5 |
| Example 5 | 5 | 8 | 55 | | 4 |
| Example 4 | 8 | 15 | 125 | | |
| Example 17 | 13 | 35 | 110 | >300 | 1 |
| Example 2 | 15 | 19 | 33 | | |
| Example 6 | 17 | 25 | 130 | | |
| Example 18 | 23 | 50 | >100 | >300 | |
| Example 20 | 14 | 22 | 70 | | |
| Example 21 | 60 | 35 | 240 | | |
| Example 22 | 80 | 6 | 180 | | |
| Example 24 | 55 | 22 | 160 | | |
| Example 25 | 62 | 4.2 | 160 | | |
| Example 26 | 80 | 15 | 150 | | |
| Example 27 | 30 | 16 | 40 | | |
| Example 28 | 15 | 10 | 110 | | |
| Example 30 | 7.5 | 5 | 33 | | |

The data shows that the 2-substituted piperidine analogs of this invention exhibit selectivity for 2A and 2B subtype receptors compared to 2C and 2D subtype receptors. Certain 2-substituted piperidine analogs also have in vivo activity as an anticonvulsant in MES experiments in mice.

What is claimed is:

1. A compound represented by the formula:

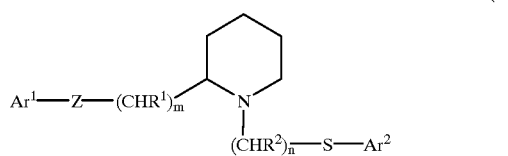

(V)

or a pharmaceutically acceptable salt thereof wherein

Ar$^1$ is a monocyclic heteroaryl group, which may be independently substituted by hydrogen, hydroxy, alkyl, a halogenated alkyl group, halogen, nitro, aryl, aralkyl, amino, a lower alkyl amino group or a lower alkoxy group;

Ar$^2$ is independently aryl or a heteroaryl group, which may be independently substituted by hydrogen, hydroxy, alkyl, a halogenated alkyl group, halogen, nitro, aryl, aralkyl, or a lower alkoxy group;

each R$^1$ is independently hydrogen, alkyl or hydroxy;
each R$^2$ is independently hydrogen, alkyl or hydroxy;
Z is —CH$_2$—, O, S or NR$^3$;
m is 0, 1 or 2; and
n is 0, 1, 2, 3, 4 or 5;

with the proviso that when Z is CH$_2$, m is 0, n is 3, and R$^2$ is hydroxy, Ar$^2$ is not halogen substituted aryl.

2. A pharmaceutical composition useful for treating disorders responsive to the selective blockade of N-methyl-D-aspartate receptor subtypes which disorders are selected from stroke, cerebral ischemia, central nervous system trauma, hypoglycemia, neurodegenerative disorders, anxiety, convulsions, aminoglycoside antibiotics-induced hearing loss, migraine headaches, chronic pain, psychosis, glaucoma, CMV retinitis, urinary incontinence, or opioid tolerance or withdrawal, said composition comprising a pharmaceutically acceptable carrier or diluent and a therapeutically acceptable carrier or diluent and an N-methyl-D-aspartate receptor antagonist effective amount of at least one compound of claim 1.

3. A method for treating disorders responsive to the selective blockade of N-methyl-D-aspartate receptor subtypes in an animal suffering therefrom which comprises administering an N-methyl-D-aspartate receptor antagonist effective amount of at least one compound represented by the formula:

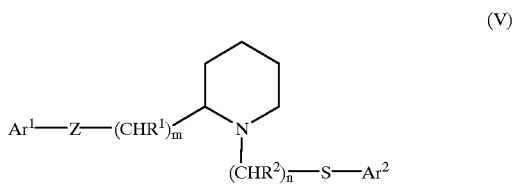

(V)

or a pharmaceutically acceptable salt thereof wherein

Ar$^1$ is a monocyclic heteroaryl group, which may be independently substituted by hydrogen, hydroxy, alkyl, a halogenated alkyl group, halogen, nitro, aryl, aralkyl, amino, a lower alkyl amino group or a lower alkoxy group;

Ar$^2$ is independently aryl or a heteroaryl group, which may be independently substituted by hydrogen, hydroxy, alkyl, a halogenated alkyl group, halogen, nitro, aryl, aralkyl, or a lower alkoxy group;

each R$^1$ is independently hydrogen, alkyl or hydroxy;
each R$^2$ is independently hydrogen, alkyl or hydroxy;
Z is —CH$_2$—, O, S or NR$^3$;
m is 0, 1 or 2; and
n is 0, 1, 2, 3, 4 or 5.

4. The method according to claim 3, wherein said disorder is stroke, cerebral ischemia, central nervous system trauma or hypoglycemia.

5. The method according to claim 3, wherein said disorder is a neurodegenerative disorder.

6. The method according to claim 3, wherein said disorder is Parkinson's disease.

7. The method according to claim 3, wherein said disorder is anxiety, convulsions or chronic pain.

8. The method according to claim 3, wherein said disorder is migraine headache.

9. The method according to claim 3, wherein said disorder is glaucoma and CMV retinitis.

10. The method according to claim 3, wherein said disorder is psychosis.

11. The method according to claim 3, wherein said disorder is urinary incontinence.

12. The method according to claim 3, wherein said disorder is opioid tolerance or withdrawal.

13. The method according to claim 3, wherein said disorder is amioglycoside antibiotics-induced hearing loss.

* * * * *

UNITED STATES PATENT AND TRADEMARK OFFICE
CERTIFICATE OF CORRECTION

PATENT NO.  :  6,124,317

DATED  :  September 26, 1996

INVENTOR(S)  :  CHRISTOPHER F. BIGGE, ET AL.

It is certified that error appears in the above-identified patent and that said Letters Patent is hereby corrected as shown below:

ON THE TITLE PAGE [56]:

>   References Cited, FOREIGN PATENT DOCUMENTS, "04217945"
>       should read --4-217945--; and
>   References Cited, OTHER PUBLICATIONS, "M. Lauritzen et
>       al., Brian Res." should read --M. Lauritzen et al.,
>       Brian Res.--.

COLUMN 3:

>   Line 55

COLUMN 5:

>   Line 9, "opt. " should read --optionally--; and
>   Line 67, Close up left margin

COLUMN 6:

>   Line 1-23, Close up left margin (lines 1-23).

COLUMN 15:

>   Line 35, "agent" should read --agents--; and
>   Line 41, "maybe" should read --may be--.

UNITED STATES PATENT AND TRADEMARK OFFICE
CERTIFICATE OF CORRECTION

PATENT NO. : 6,124,317

DATED : September 26, 1996

INVENTOR(S) : CHRISTOPHER F. BIGGE, ET AL.

It is certified that error appears in the above-identified patent and that said Letters Patent is hereby corrected as shown below:

COLUMN 16:

Line 60, "migrane" should read --migraine--.

COLUMN 19:

Line 56, "$I/I_{control} = 1/(1+([antagonist]/10^{-pIC50})^n$" should read --$I/I_{control} = 1/(1+ ([antagonist]/10^{-pIC50})^n)$--."

COLUMN 24:

Line 62, "HBr" should read --The HBr--.

COLUMN 25:

Line 16, "ref lux" should read --reflux--;
Line 19, "3x50" should read --(3 x 50--; and
Line 55, "bases" should read --base--.

COLUMN 30:

Line 21, "HZ," should read --Hz,--.

COLUMN 31:

Line 43, "PtO2" should read --$PtO_2$--.

COLUMN 32:

Line 27, "15." should be deleted.

UNITED STATES PATENT AND TRADEMARK OFFICE
CERTIFICATE OF CORRECTION

PATENT NO. : 6,124,317

DATED : September 26, 1996

INVENTOR(S) : CHRISTOPHER F. BIGGE, ET AL.

It is certified that error appears in the above-identified patent and that said Letters Patent is hereby corrected as shown below:

COLUMN 34:

Line 2, "yeild" should read --yield--;
    Line 34, "(m.1H)," should read --(m, 1H),--;
    Line 55, "evapoated," should read --evaporated,--; and
    Line 61, "NH2)," should read --NH$_2$),--.

Signed and Sealed this

Twenty-second Day of May, 2001

Attest:

NICHOLAS P. GODICI

Attesting Officer     Acting Director of the United States Patent and Trademark Office